United States Patent
Oxford et al.

(10) Patent No.: US 8,242,127 B2
(45) Date of Patent: *Aug. 14, 2012

(54) DERIVATIVES OF PYRIMIDO[6,1-A]ISOQUINOLIN-4-ONE

(75) Inventors: Alexander William Oxford, Hertfordshire (GB); David Jack, Hertfordshire (GB)

(73) Assignee: Verona Pharma plc, London (GB)

( * ) Notice: Subject to any disclaimer, the term of this patent is extended or adjusted under 35 U.S.C. 154(b) by 999 days.

This patent is subject to a terminal disclaimer.

(21) Appl. No.: 12/150,232

(22) Filed: Apr. 24, 2008

(65) Prior Publication Data

US 2008/0206163 A1    Aug. 28, 2008

Related U.S. Application Data

(60) Continuation of application No. 10/786,400, filed on Feb. 24, 2004, now Pat. No. 7,378,424, which is a division of application No. 09/964,260, filed on Sep. 26, 2001, now Pat. No. 6,794,391, which is a continuation of application No. PCT/GB00/01193, filed on Mar. 29, 2000.

(30) Foreign Application Priority Data

Mar. 31, 1999  (GB) .................................. 9907454.4
Apr. 28, 1999  (GB) .................................. 9909802.2

(51) Int. Cl.
*A01N 43/54*    (2006.01)
*A61K 31/505*   (2006.01)

(52) U.S. Cl. ........................................ 514/267; 544/252
(58) Field of Classification Search .......................... None
See application file for complete search history.

(56) References Cited

U.S. PATENT DOCUMENTS

| | | | |
|---|---|---|---|
| 4,254,118 A | 3/1981 | Gauthier et al. | |
| 4,254,121 A | 3/1981 | Gauthier et al. | |
| 4,307,092 A | 12/1981 | Gauthier et al. | |
| 4,400,506 A | 8/1983 | Lal et al. | |
| 4,581,172 A | 4/1986 | Kaiser et al. | |
| 5,141,936 A | 8/1992 | Rupp et al. | |
| 6,794,391 B2 * | 9/2004 | Oxford et al. | 514/267 |

FOREIGN PATENT DOCUMENTS

GB    1 597 717    9/1981

OTHER PUBLICATIONS

Borisy, et. al., Proceedings of the National Academy of Sciences of the United States of America, 100(13) 7977-7982.*
B. Lal et al., "Trequinsin, a Potent New Antihypertensive Vasodilator", *J. Med. Chem.*, vol. 27, No. 11, pp. 1470-1480 (1984).
J.O. Odingo, "Inhibitors of PDE4: A review of recent patent literature", *Expert Opin. Ther. Patents* (2005), vol. 15, No. 7, pp. 773-787.

* cited by examiner

*Primary Examiner* — Jeffrey Murray
(74) *Attorney, Agent, or Firm* — Peter F. Corless; Christine C. O'Day; Edwards Wildman Palmer LLP

(57) ABSTRACT

The present invention relates to derivatives of pyrimido[6,1-a]isoquinolin-4-one and their application as inhibitors of phosphodiesterase (PDE) isoenzymes. More particularly the invention relates to derivatives of pyrimido[6,1-a]isoquinolin-4-one and their use in medicine for example as bronchodilators with anti-inflammatory properties.

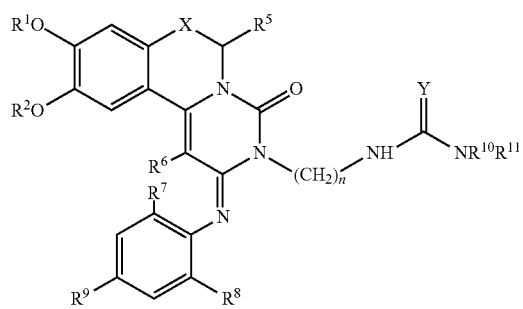

(I)

8 Claims, 5 Drawing Sheets

DERIVATIVES OF PYRIMIDO[6,1-A]ISOQUINOLIN-4-ONE

Figure 1:
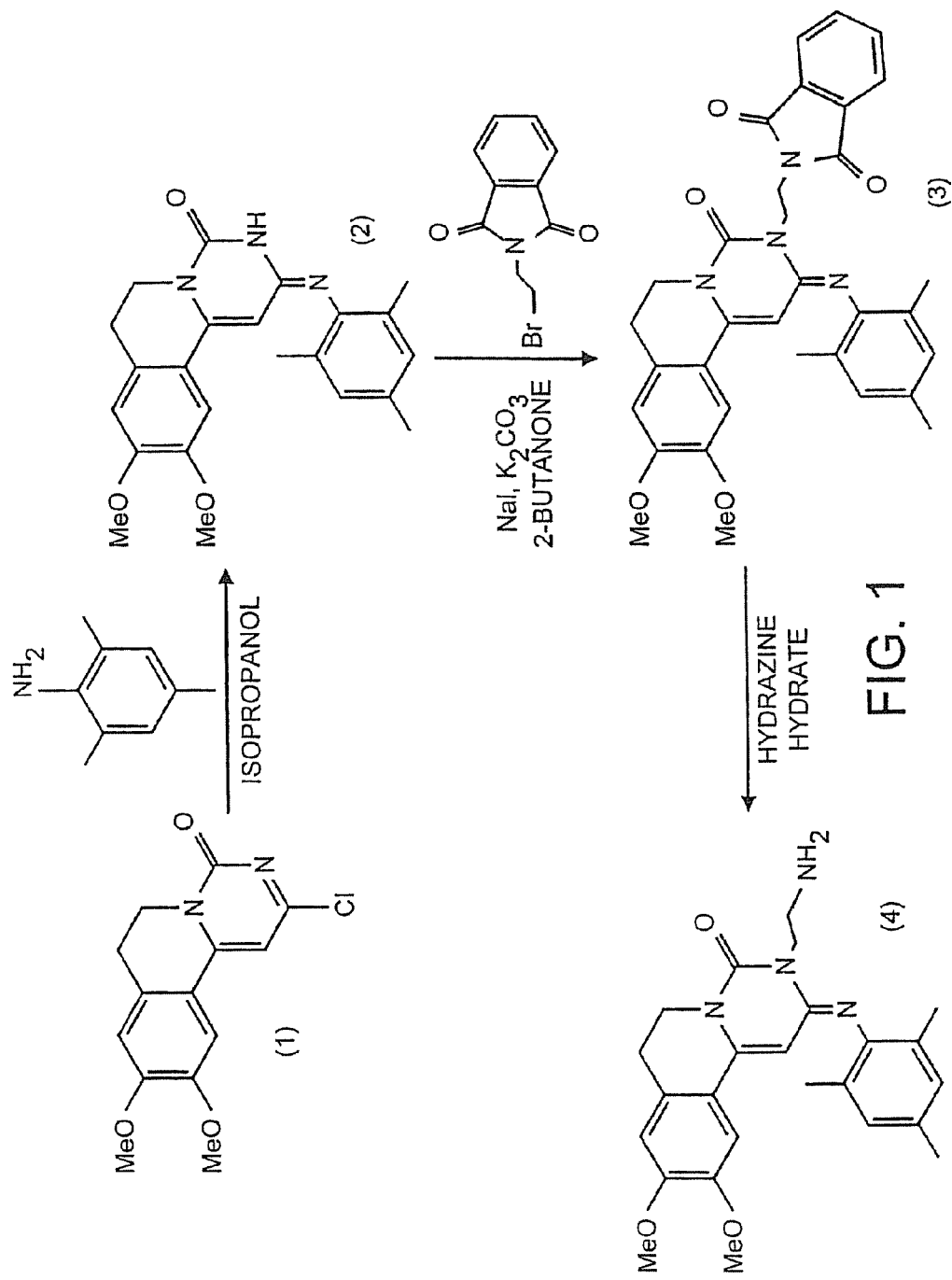

The present invention relates to derivatives of pyrimido[6,1-a]isoquinolin-4-one and their application as inhibitors of phosphodiesterase (PDE) isoenzymes. More particularly the invention relates to derivatives of pyrimido[6,1-a]isoquinolin-4-one and their use in medicine for example as bronchodilators with anti-inflammatory properties.

In all cells where cyclic AMP (cAMP) is present as a secondary messenger, intracellular concentrations of cAMP are regulated by the two processes involved in its formation and degradation. Stimulation of membrane bound receptors on the external surface of the cells (e.g. by β-adrenoceptor agonists) results in activation of adenylyl cyclase to generate cAMP from ATP. Phosphodiesterases present in the cell serve to reduce the concentration of cAMP by hydrolysing it to adenosine monophosphate (AMP).

In a disease such as asthma, the principal cells involved in the associated bronchoconstriction and inflammatory processes are subject to inhibitory control by cAMP. Inhibitors of type III phosphodiesterase raise intracellular levels of cAMP, leading to relaxation of bronchial smooth muscle, whereas inhibitors of type IV phosphodiesterase inhibit the release of damaging mediators from pro-inflammatory cells. Thus, in principle, a combined PDE III/IV inhibitor should have the desirable effects of a β-adrenoceptor agonist plus an inhaled anti-inflammatory steroid which are currently the mainstay of treatment in severe asthma. Moreover, a combined PDE III/IV inhibitor given by inhalation should achieve beneficial effects similar to a agonist plus inhaled steroid and should be an unusually effective treatment of asthma and other respiratory disorders without the undesirable glucocorticoid effects of the steroid such as osteoporosis and the stunting of growth.

The potential adverse effects of a PDE III/IV inhibitor (e.g. nausea and vomiting, gastric acid secretion, cardiovascular effects such as increased cardiac contractility, vasodilation and potential arrhythmogenic activity) should be avoidable with a compound that is delivered directly to the lungs by inhalation. It is desirable that the substance is long acting, non irritant and has a taste which is not so unpleasant as to have any adverse effect on patient compliance.

An example of a pyrimido[6,1-a]isoquinolin-4-one derivative with PDE III/IV inhibitory activity and known to possess antihypertensive vasodilator activity is trequinsin (9,10-dimethoxy-3-methyl-2-mesitylimino-2,3,6,7-tetrahydro-4H-pyrimido[6,1-a]isoquinolin-4-one), which is described by De Souza et al., *J. Med. Chem.* 27 1470-1480 (1984) and in GB-A-1597717.

As described by De Souza et al. and in GB-A-1597717, trequinsin has valuable pharmacological properties, and can be administered to human subjects suffering from, for example, respiratory disorders. However, it is unsuitable for administration by inhalation because of its bitter taste and in vitro data indicate its persistence of action is less than desirable.

It has now been found that it is possible to design certain pyrimido[6,1-a]isoquinolin-4-one derivatives which are PDE inhibitors, which have a longer duration of action relative to trequinsin and other useful properties, such as improved taste.

According to a first aspect of the present invention there is provided a compound of general formula I:

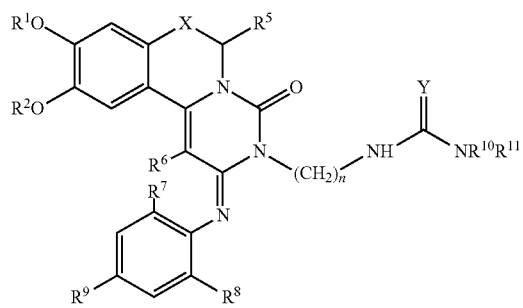

wherein
each of $R^1$ and $R^2$ independently represents a $C_{1-6}$ alkyl or $C_{2-7}$ acyl group;
$R^5$ represents a hydrogen atom or a $C_{1-3}$ alkyl, $C_{2-3}$ alkenyl or $C_{2-3}$ alkynyl group;
$R^6$ represents a hydrogen atom or a $C_{1-6}$ alkyl, $C_{2-6}$ alkenyl, $C_{2-6}$ alkynyl, amino, $C_{1-6}$ alkylamino, di($C_{1-6}$)alkylamino or $C_{2-7}$ acylamino group;
each of $R^7$ and $R^8$ independently represents a hydrogen or halogen atom or a hydroxy, trifluoromethyl, $C_{1-6}$ alkyl, $C_{2-6}$ alkenyl, $C_{2-6}$ alkynyl, $C_{2-7}$ acyl, $C_{1-6}$ alkylthio, $C_{1-6}$ alkoxy, $C_{3-6}$ cycloalkyl; and
$R^9$ represents a hydrogen or halogen atom or a hydroxy, trifluoromethyl, $C_{1-6}$ alkyl, $C_{2-6}$ alkenyl, $C_{2-6}$ alkynyl, $C_{2-7}$ acyl, $C_{1-6}$ alkylthio, $C_{1-6}$ alkoxy or $C_{3-6}$ cycloalkyl group;
X represents $OCH_2$ or a group $CR^3R^4$, wherein each of $R^3$ and $R^4$ independently represents a hydrogen atom or a $C_{1-3}$ alkyl group;
each of $R^{10}$ and $R^{11}$ independently represents a hydrogen atom, a $C_{1-3}$ alkyl, $C_{3-6}$ cycloalkyl or phenyl group;
Y represents an oxygen atom or a group $CHNO_2$, NCN, NH or $NNO_2$;
n is an integer from 2 to 4;
or a salt thereof.

As used herein the term "halogen" or its abbreviation "halo" means fluoro, chloro, bromo or iodo.

As used herein the term "$C_{1-6}$ alkyl" refers to straight chain or branched chain alkyl groups having from one to six carbon atoms. Illustrative of such alkyl groups are methyl, ethyl, propyl, isopropyl, butyl, isobutyl, sec-butyl, tert-butyl, pentyl, neopentyl and hexyl. $C_{1-4}$ alkyl groups are preferred.

As used herein the term "$C_{2-3}$ alkenyl" refers to straight chain or branched chain hydrocarbon groups having from two to three carbon atoms and having in addition one double bond, of either E or Z stereochemistry where applicable. This term would include for example, vinyl and 1-propenyl.

As used herein the term "$C_{2-3}$ alkynyl" refers to straight chain hydrocarbon groups having from two to three carbon atoms and having in addition one triple bond. This term would include for example, ethynyl and 1-propynyl.

As used herein the term "$C_{2-6}$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl. $C_{2-3}$ alkenyl groups are preferred.

As used herein the term "$C_{2-6}$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentanyl, 3-pentanyl, 4-pentanyl, 2-hexanyl, 3-hexanyl, 4-hexanyl and 5-hexanyl. $C_{2-3}$ alkynyl groups are preferred.

As used herein the term "$C_{1-6}$ alkoxy" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy. $C_{1-4}$ alkoxy groups are preferred.

As used herein the term "$C_{2-7}$ acyl" refers to straight chain or branched chain acyl groups having from two to seven carbon atoms. Illustrative of such acyl groups are acetyl, propionyl (or propiono or propanoyl), isopropionyl (or isopropiono or isopropanoyl), butyryl (or butanoyl), isobutyryl (or isobutanoyl), pentanoyl (or valeryl), hexanoyl (or capronyl) and heptanoyl.

As used herein the term "$C_{2-7}$ acyloxy" refers to straight chain or branched chain acyloxy groups having from two to seven carbon atoms. Illustrative of such acyloxy groups are acetyloxy, propionyl (or propiono or propanoyl)oxy, isopropionyl (or isopropiono or isopropanoyl)oxy, butyryl (or butanoyl)oxy, isobutyryl (or isobutanoyl)oxy, pentanoyl (or valeryl)oxy, hexanoyl (or capronyl)oxy and heptanoyloxy. $C_{2-4}$ acyloxy groups are preferred.

As used herein the term "$C_{3-6}$ cycloalkyl" refers to an alicyclic group having from three to six carbon atoms. Illustrative of such cycloalkyl groups are cyclopropyl, cyclobutyl, cyclopentyl and cyclohexyl. Cyclopentyl and cyclohexyl groups are preferred.

As used herein the term "$C_{1-6}$ alkylthio" refers to straight chain or branched chain alkylthio groups having from one to six carbon atoms. Illustrative of such alkylthio groups are methylthio, ethylthio, propylthio, isopropylthio, butylthio, isobutylthio, sec-butylthio, tert-butylthio, pentylthio, neopentylthio and hexylthio. $C_{1-4}$ alkylthio groups are preferred.

As used herein the term "$C_{1-6}$ alkylamino" refers to straight chain or branched chain alkylamino groups having from one to six carbon atoms. Illustrative of such alkylamino groups are methylamino, ethylamino, propylamino, isopropylamino, butylamino, isobutylamino, sec-butylamino, tert-butylamino, pentylamino, neopentylamino and hexylamino. $C_{1-4}$ alkylamino groups are preferred.

As used herein, the term "di($C_{1-6}$)alkylamino" refers to straight chain or branched chain di-alkylamino groups having from one to six carbon atoms in each of the alkyl groups. Illustrative of such dialkylamino groups are di-methylamino, di-ethylamino, di-propylamino, di-isopropylamino, di-butylamino, di-isobutylamino, di-sec-butylamino, di-tert-butylamino, di-pentylamino, di-neopentylamino and di-hexylamino. Di($C_{1-4}$)alkylamino groups are preferred.

As used herein, the term "$C_{2-7}$ acylamino" refers to straight chain or branched chain acylamino groups having from two to seven carbon atoms. Illustrative of such acylamino groups are acetylamino, propionyl (or propiono or propanoyl)amino, isopropionyl (or isopropiono or isopropanoyl)amino, butyryl (or butanoyl)amino, isobutyryl (or isobutanoyl)amino, pentanoyl (or valeryl)amino, hexanoyl (or capronyl)amino and heptanoylamino. $C_{2-4}$ acylamino groups are preferred.

Where there is a substituent which renders a compound basic, for example when $R^6$ is an amino, alkylamino or dialkylamino group, addition of an acid results in a salt. The acid may be any suitable acid, and can be organic or inorganic.

Preferred compounds of general formula I include those in which, independently or in any compatible combination:
each of $R^1$ and $R^2$ represents a $C_{1-6}$ alkyl, preferably a $C_{1-4}$ alkyl, group;

$R^1$ and $R^2$ are the same as each other;

each of $R^3$ and $R^4$ represents a hydrogen atom;

$R^5$ represents a hydrogen atom;

$R^6$ represents a hydrogen atom;

each of $R^7$ and $R^8$ represents a $C_{1-6}$ alkyl, preferably methyl, ethyl or isopropyl, group;

$R^7$ and $R^8$ are the same as each other;

$R^9$ represents a hydrogen atom, a halogen atom or a methyl or acetyl group;

Y represents an oxygen atom or a group $CHNO_2$; and n is 2.

Exemplary compounds include:

1. 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one;
2. 9,10-Dimethoxy-2-(2,4,6-trimethylphenylimino)-3-[N—(N'-isopropylcarbamoyl)-2-aminoethyl]-3,4,6,7-tetrahydro-2H-pyrimido[6,1-a]isoquinolin-4-one;
3. 9,10-Dimethoxy-2-(2,4,6-trimethylphenylimino)-3-[N-[1-(N'-methyl-2-nitroethenamine)]-2-aminoethyl]-3,4,6,7-tetrahydro-2H-pyrimido[6,1-a]-isoquinolin-4-one;
4. 9,10-Dimethoxy-2-(2,4,6-trimethylphenylimino)-3-[N-[1-(N'-isopropyl-2-nitroethenamine)]-2-aminoethyl]-3,4,6,7-tetrahydro-2H-pyrimido[6,1-a]-isoquinolin-4-one;
5. 9,10-Dimethoxy-2-(2,4,6-trimethylphenylimino)-3-[N-[1-(N',N'-dimethyl-2-nitroethenamine)]-2-aminoethyl]-3,4,6,7-tetrahydro-2H-pyrimido[6,1-a]-isoquinolin-4-one;
6. 9,10-Dimethoxy-2-(2,4,6-trimethylphenylimino)-3-[N—(N'-phenylcarbamoyl)-2-aminoethyl]-3,4,6,7-tetrahydro-2H-pyrimido[6,1-a]isoquinolin-2-one;
7. 9,10-Dimethoxy-3-[2-guanidinoethyl]-2-(2,4,6-trimethylphenylimino)-3,4,6,7-tetrahydro-2H-pyrimido[6,1-a]isoquinolin-4-one;
8. 9,10-Dimethoxy-3-[N—(N-nitro)-2-guanidinoethyl]-2-(2,4,6-trimethylphenylimino)-3,4,6,7-tetrahydro-2H-pyrimido[6,1-a]isoquinolin-4-one;
9. 3-[N—(N'-Cyclohexylcarbamoyl)-2-aminoethyl]-9,10-dimethoxy-2-(2,4,6-trimethyl-phenylimino-3,4,6,7-tetrahydro-2H-pyrimido[6,1-a]isoquinolin-4-one;
10. 3-(N-Carbamoyl-2-aminoethyl)-9,10-dimethoxy-2-(2-methylphenylimino)-3,4,6,7-tetrahydro-2H-pyrimido[6,1-a]isoquinolin-4-one;
11 3-(N-Carbamoyl-2-aminoethyl)-2-(2,6-diisopropylphenylimino)-9,10-dimethoxy-3,4,6,7-tetrahydro-2H-pyrimido[6,1-a]isoquinolin-4-one;
12. 3-(N-Carbamoyl-4-aminobutyl)-9,10-dimethoxy-2-(2,4,6-trimethylphenylimino)-3,4,6,7-tetrahydro-2H-pyrimido[6,1-a]isoquinoiin-4-one;
13. 3-[N—(N'-Cyano-N"-methyl)-2-guanidinoethyl]-9,10-dimethoxy-2-(2,4,6-trimethyl-phenylimino)-3,4,6,7-tetrahydro-2H-pyrimido[6,1-a]isoquinolin-4-one.

The compound: 9,10-Dimethoxy-2-(2,4,6-trimethylphenylimino)-3-(N-carbamoyl amino ethyl)-3,4,6,7 tetrahydro-2H-pyrimido[6,1-a]isoquinolin-4-one is particularly preferred.

Compounds of general formula I may be prepared by any suitable method known in the art and/or by the following process, which itself forms part of the invention.

According to a second aspect of the invention, there is provided a process for preparing a compound of general formula I as defined above, the process comprising:
(a) derivatising a compound of general formula II:

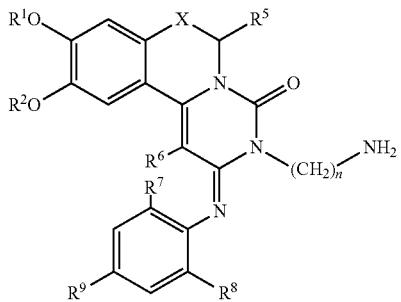

II wherein $R^1$, $R^2$, $R^5$, $R^6$, $R^7$, $R^8$, $R^9$, X and n are as defined for general formula I, with one or more compounds capable of reacting at the primary amine group of the aminoalkyl moiety (—$(CH_2)_n$—$NH_2$), to form a compound of general formula I; or
(b) when X in general formula I represents a group $CR^3R^4$, wherein $R^3$ represents a hydrogen atom, $R^4$ represents a hydrogen atom or a $C_{1-3}$ alkyl group, and $R^5$ represents a hydrogen atom or a $C_{1-3}$ alkyl group, hydrogenating a compound of general formula III:

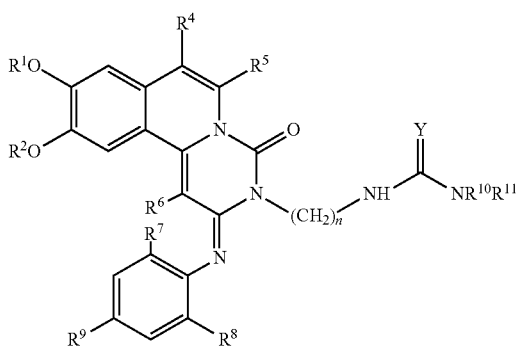

III wherein $R^1$, $R^2$, $R^6$, $R^7$, $R^8$, $R^9$, $R^{10}$, $R^{11}$, Y and n are as defined for general formula I; and
(c) optionally converting a compound of general formula I so formed into another compound of general formula I.

The reaction conditions of step (a) are generally such as to favour the reaction, which may be a nucleophilic displacement or addition and is carried out in a solvent which is suitable for the particular reaction.

Compounds chosen for reacting with a compound of general formula II are capable of reacting at the primary amine group of the alkylamino moiety in the compound of general formula II, to form a compound of general formula I. For example:
when Y represents an oxygen atom and each of $R^{10}$ and $R^{11}$ represents a hydrogen atom, a compound of general formula II may be derivatised with sodium cyanate;
when Y represents an oxygen atom, $R^{10}$ represents a hydrogen atom and $R^{11}$ represents a $C_{1-3}$ alkyl, $C_{3-6}$ cycloalkyl or phenyl group, a compound of general formula II may be derivatised with an isocyanate of the general formula $R^{11}NCO$;

when Y represents $CHNO_2$, $R^{10}$ represents a hydrogen atom and $R^{11}$ represents a $C_{1-3}$ alkyl or $C_{3-6}$ cycloalkyl group, a compound of general formula II may be derivatised with an N—$C_{1-3}$ alkyl- or N—$C_{3-6}$ cycloalkyl-1-(methylthio)-2-nitroethenamine of the general formula $CH_3SC(=CHNO_2)NR^{10}R^{11}$;
when Y represents $CHNO_2$, a compound of general formula II may be reacted first with 1,1-bis(methylthio)-2-nitroethylene and the resulting compound may then be reacted with an amine of the general formula $R^{10}R^{11}NH$, wherein $R^{10}$ and $R^{11}$ are as defined for general formula I;
when Y represents NH, a compound of general formula II may be derivatised with a compound of general formula $CH_3SC(=NH)NR^{10}R^{11}$ or a salt thereof, wherein $R^{10}$ and $R^{11}$ are as defined for general formula I; and
when Y represents NCN, a compound of general formula II may be derivatised with a compound of general formula $CH_3SC(=NCN)NR^{10}R^{11}$ or a salt thereof, wherein $R^{10}$ and $R^{11}$ are as defined for general formula I.

In specific cases:
for 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one, sodium cyanate may be chosen;
for 9,10-Dimethoxy-2-(2,4,6-trimethylphenylimino)-3-[N—(N'-isopropylcarbamoyl)-2-aminoethyl]-3,4,6,7-tetrahydro-2H-pyrimido[6,1-a]isoquinolin-4-one, isopropylisocyanate may be chosen;
for 9,10-Dimethoxy-2-(2,4,6-trimethylphenylimino)-3-[N—[1-(N'-methyl-2-nitroethenamine)]-2-aminoethyl]-3,4,6,7-tetrahydro-2H-pyrimido[6,1-a]-isoquinolin-4-one, N-methyl-1-(methylthio)-2-nitroethenamine may be chosen;
for 9,10-Dimethoxy-2-(2,4,6-trimethylphenylimino)-3-[N—[1-(N'-isopropyl-2-nitroethenamine)]-2-aminoethyl]-3,4,6,7-tetrahydro-2H-pyrimido[6,1-a]-isoquinolin-4-one, 1,1-bis(methylthio)-2-nitroethylene and isopropylamine may be chosen;
for 9,10-Dimethoxy-2-(2,4,6-trimethylphenylimino)-3-[N—[1-(N',N'-dimethyl-2-nitroethenamine)]-2-aminoethyl]-3,4,6,7-tetrahydro-2H-pyrimido[6,1-a]isoquinolin-4-one, 1,1-bis(methylthio)-2-nitroethylene and dimethylamine may be chosen; and
for 9,10-Dimethoxy-2-(2,4,6-trimethylphenylimino)-3-[N—(N'-phenylcarbamoyl)-2-aminoethyl]-3,4,6,7-tetrahydro-2H-pyrimido[6,1-a]isoquinolin-2-one, phenylisocyanate may be chosen.

Compounds of general formula II may be prepared by reacting a compound of general formula IV:

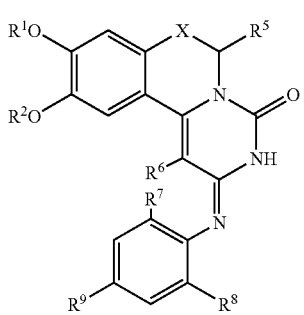

IV wherein $R^1$, $R^2$, $R^5$, $R^6$, $R^7$, $R^8$, $R^9$ and X are as defined for general formula I, with a compound of general formula V:

LG-$(CH_2)_n$—N—PG    V wherein n is as defined for general formula I, LG represents a leaving group, and PG represents a protecting group; and then removing the protecting group.

The reaction between a compound of general formula IV and a compound of general formula V is generally carried out in suitable conditions for the reaction, which is a nucleophilic substitution. A base such as $K_2CO_3$ may be used in the presence of NaI and the reaction is performed in a suitable solvent such as 2-butanone.

The leaving group LG in general formula V may be any suitable leaving group, but is preferably a halogen atom, such as bromine. The protecting group PG in general formula V may be any suitable protecting group, such as a phthaloyl group. If the reaction between a compound of general formula IV and V is carried out in a base such as $K_2CO_3$, the protecting group should be base-stable. A suitable compound of general formula V is N-(2-bromoethyl)phthalimide:

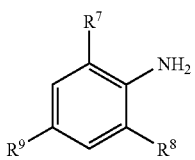

The protecting group may then be removed by standard deprotection procedures. For example, hydrazine hydrate may be used. The reaction conditions are generally to favour the reaction, for example in a suitable solvent such as ethanol and/or chloroform at room temperature.

Compounds of general formula IV may be prepared by reacting a compound of general formula VI:

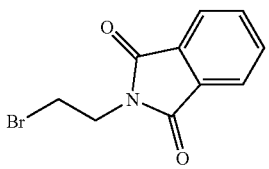

VI wherein $R^1$, $R^2$, $R^5$, $R^6$ and X are as defined for general formula I and LG represents a leaving group; with a compound of general formula VII:

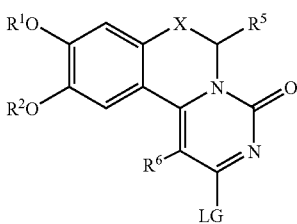

VII wherein $R^7$, $R^8$ and $R^9$ are as defined for general formula I.

Compounds of general formula VII are substituted anilines which are either known in the art and available from commercial sources or may readily be prepared by methods known per se.

The leaving group LG in compounds of general formula VI may be chlorine, a thioalkyl group, preferably thiomethyl, or an alkylsulphonyl group, preferably methylsulphonyl. Preferably it is chlorine.

The reaction conditions are generally such as to favour the reaction, which is a nucleophilic displacement which is preferably carried out in a suitable solvent such as dimethylformamide or isopropanol in the presence of a base such as potassium carbonate. Suitable reaction conditions may be found in GB-A-1597717 and EP-A-0124893, which disclose the preparation of related compounds.

The reaction is generally applicable for producing compounds of general formula I where $R^6$ represents a hydrogen atom or a $C_{1-6}$ alkyl, $C_{2-6}$ alkenyl, $C_{2-6}$ alkynyl, amino, $C_{1-6}$ alkylamino or $C_{2-7}$ acylamino group and $R^1$ to $R^5$ and $R^7$ to $R^9$, X, Y and n have the meanings given above.

Compounds of general formula VI where LG represents a chlorine atom may be prepared by reacting a compound of general formula VIII or a compound of general formula IX with phosphorous oxychloride, or by heating a compound of general formula VIII with phosphorous pentachloride:

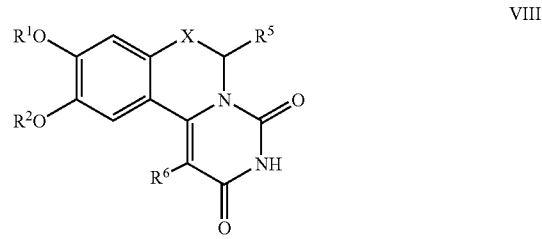

VIII

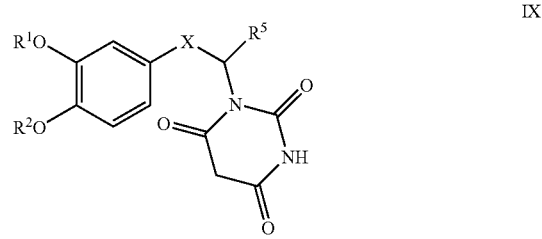

IX wherein $R^1$, $R^2$, $R^5$ and $R^6$ and X are as defined for general formula I. Compounds of general formula VI where LG represents a thioalkyl group may be prepared from compounds of formula VIII by heating with phosphorous pentasulphide in a solvent such as dioxan or pyridine to give initially the intermediate thio derivative of VIII which, on treatment with an alkylating agent such as an alkyl iodide eg. methyl iodide, in a suitable solvent such as tetrahydrofuran or ethyl acetate, gives the thioalkyl compound. Oxidation of the thioalkyl compound with, for example, 3-chloroperbenzoic acid in a solvent such as methylene chloride, gives the alkylsulphone derivative.

Compounds of general formula VIII may be prepared by reacting a compound of general formula IX, wherein $R^1$, $R^2$, $R^5$ and $R^6$ are as defined for general formula I, with a cyclodehydrating agent such as phosphorous oxychloride, under less vigorous condition, ie lower temperatures, than those required to give compounds of the general formula VI where LG represents a chlorine atom. An alternative method has been described in NL-A-6,401,827 (Hoffmann-La Roche) which involves reacting the carbamoylmethylene-tetrahydroisoquinoline, general formula XI (wherein $R^1$, $R^2$, $R^5$ and X have the meanings given above) with diethyl carbonate in ethanolic sodium ethoxide:

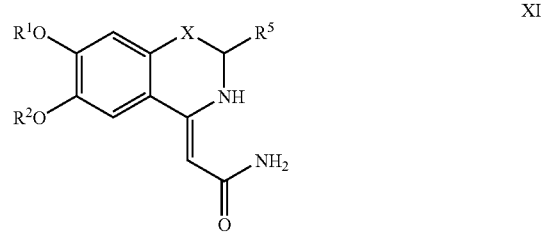

XI

Compounds of general formula IX may be prepared by reacting a compound of general formula XII

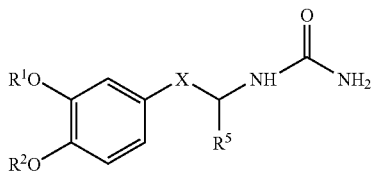

XII wherein $R^1$, $R^2$, $R^5$ and X are as defined for general formula I, with $R^6CH(CO_2Et)_2$, wherein $R^6$ is as defined for general formula I, and a strong base such as sodium ethoxide in a hot ethanolic solution. Alternatively, the corresponding dimethyl ester can be employed in the presence of hot methanolic sodium methoxide.

Compounds of general formula XII may be prepared by reacting a compound of general formula XIII:

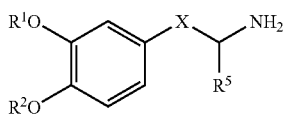

XIII wherein $R^1$, $R^2$, $R^5$ and X are as defined for general formula I, with urea by heating at 160° C. Alternatively, compounds of general formula XIII may be reacted with potassium cyanate in the presence of acetic acid in a suitable solvent such as ethanol.

Compounds of general formula XIII are either known in the art or may readily be prepared by methods known per se. For example, the preparation of 1-(3,4-dimethoxyphenethyl) barbituric acid has been described by B. Lal et al. in *J. Med. Chem.* 27 1470-1480 (1984).

Turning to step (b), the reaction conditions of step (b) are generally to favour the hydrogenation reaction, and the reaction is generally carried out in a suitable solvent such as an alcohol, eg ethanol, with a noble metal catalyst such as palladium, platinum, rhodium or nickel, at room temperature. The catalyst may be supported, for example on charcoal or alumina.

Compounds of general formula III may be prepared from a compound of general formula XIV:

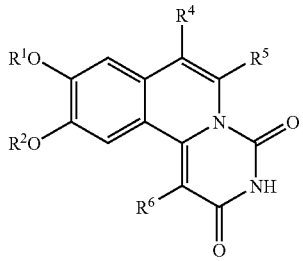

XIV wherein $R^1$, $R^2$ and $R^6$ are as defined for general formula I, and $R^4$ and $R^5$ independently represent a hydrogen atom or a $C_{1-3}$ alkyl group. The reactions are conducted as described above for converting a compound of general formula VIII to a compound of general formula II through compounds of general formula VI and general formula IV, and the preferred reaction conditions correspond accordingly.

Compounds of general formula XIV may be prepared from compounds of general formula VIII (wherein X represents a $CH_2$ group and $R^5$ represents a hydrogen atom or a $C_{1-3}$ alkyl group) by heating with a noble metal catalyst such as palladium, platinum, rhodium or nickel at a temperature of 300 to 350° C. The catalyst may be supported on charcoal or alumina and the reaction carried out in an inert solvent such as an aromatic hydrocarbon, eg p-cymene.

In optional step (c), a compound of general formula I may be converted into another compound of general formula I. For example, compounds of general formula I where $R^6$ represents $NH_2$ may be converted into compounds of general formula I where $R^6$ represents a $C_{1-6}$ alkylamino group by standard chemistry, such as by alkylation of a protected derivative such as an acyl or a p-toluenesulphonyl derivative followed by removal of the protecting group, such as by acid hydrolysis. Compounds of general formula I where $R^6$ represents a di($C_{1-6}$)alkylamino group may be prepared by direct alkylation of the alkylamino derivative. Compounds of general formula I wherein $R^5$, $R^6$, $R^7$, $R^8$ and/or $R^9$ represent a $C_{2-3}$ alkenyl, $C_{2-6}$ alkenyl, $C_{2-3}$ alkynyl or $C_{2-6}$ alkynyl group may be hydrogenated to give the corresponding compound with saturated bonds. The reaction conditions for the hydrogenation are as outlined above for step (b).

According to a third aspect, the present invention provides a composition comprising a compound of general formula I and a veterinarily or pharmaceutically acceptable carrier or diluent. Preferably the composition is a pharmaceutical composition for human medicine.

Compounds of the present invention are PDE inhibitors and thus possess valuable pharmacological properties, such as bronchodilator activity as demonstrated by the inhibition of field-stimulated contraction of guinea-pig isolated trachea, and anti-inflammatory activity as illustrated in studies on human mononuclear cells stimulated by PHA (phytohaemagglutinin). In vitro and in vivo data indicate the compounds have a long duration of action, as demonstrated by their persistent protective effects against histamine induced bronchospasm in the guinea-pig when inhaled directly into the lungs as a dry powder. The invention therefore also relates to acute, chronic or prophylactic treatment of patients suffering from respiratory disorders including, in particular, asthma, allergic asthma, hay fever, allergic rhinitis, bronchitis, chronic obstructive pulmonary disease (COPD), adult respiratory distress syndrome (ARDS), and cystic fibrosis. They may also be used topically in skin disorders such as atopic dermatitis and psoriasis, or in ocular inflammation or any other disease including cerebral ischaemia or auto-immune diseases in which increasing intracellular concentrations of cAMP is considered beneficial.

One or more compounds as set out in the first aspect of the invention may be present in association with one or more non-toxic pharmaceutically and/or veterinarily acceptable carriers and/or diluents and/or adjuvants and/or propellants and, if desired, other active ingredients. Suitable carriers or diluents are known in the art (eg *Handbook of Pharmaceutical Excipients* (1994) $2^{nd}$ Edition, Eds. A. Wade./P J Weller, The Pharmaceutical Press, American Pharmaceutical Association).

Preferably, the compounds and the compositions of the present invention are administered by inhalation, for example by aerosols or sprays which can disperse the pharmacological active ingredient in the form of a powder or in the form of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or wetting agent to form a stable dispersion. Pharmaceutical compositions in which the pharmacological active ingredient is in solution contain, in addition to this, a suitable propellant, and furthermore, if necessary, an additional solvent and/or a stabiliser. Instead of the propellant, compressed air can also be use, it being possible for this to be produced as required by means of a suitable compression and expansion device. Pharmaceutical compositions may also be delivered by breath activated inhalation devices. Dry powder compositions are preferred for administration by inhalation.

According to a fourth aspect, the present invention provides a compound of general formula I or a composition containing a compound of general formula I for use in medicine.

Compounds of the present invention are useful as inhibitors of phosphodiesterase isoenzymes. The compounds or compositions of the present invention may be used to prevent or treat any disease in which the compounds or compositions are useful, but particularly a disease in which raising the intracellular concentration of cAMP is desirable. Examples of diseases against which compounds are useful include respiratory disorders including, in particular, asthma, bronchitis, chronic obstructive pulmonary disease (COPD), adult respiratory distress syndrome (ARDS), allergic asthma, hay fever, allergic rhinitis, and cystic fibrosis. They may also be used topically in skin disorders such as atopic dermatitis or psoriasis, ocular inflammation, or any other disease including cerebral ischaemia or auto-immune diseases in which increasing intracellular concentrations of cAMP is considered beneficial.

This aspect of the invention is particularly relevant to the treatment of humans, but is also applicable to general veterinary industry, in particular domestic animals such as dogs and cats and farm animals such as horses, pigs, cattle, sheep, etc.

Dosage levels of the order of about 0.02 mg to about 200 mg, to be taken up to three times daily, are useful in the treatment of the above-mentioned conditions. More particularly, a dosage range of about 0.2 mg to about 20 mg, taken up to three times daily, is effective. The particular dosage regime will however ultimately be determined by the attending physician and will take into consideration such factors as the medication being used, age, weight, severity of symptoms and/or severity of treatment being or to be applied, method of administration of the medication, adverse reactions and/or other contraindications.

The medication according to this aspect of the invention may be given to a patient together with other active agents, which may for example be a different compound of the present invention, or other compounds. Examples include $\beta_2$-adrenoceptor agonists, topical glucocorticoid steroids, xanthine derivatives, antihistamine compounds, leukotriene antagonists, inhibitors of leukotriene synthesis and/or combinations thereof.

According to a fifth aspect, the present invention provides the use of a compound of general formula I in the manufacture of an inhibitor of a type III/IV phosphodiesterase isoenzyme. The invention encompasses the use of a compound of general formula I in the manufacture of a bronchodilator and/or an anti-asthmatic medication and/or a medicament for the prevention or treatment of chronic obstructive pulmonary disease (COPD).

The invention also relates to a method for the treatment or prevention of a disease in a mammal where a phosphodiesterase isoenzyme inhibitor and/or a bronchodilator would be expected to be of benefit, which method comprises administering to said mammal an amount of an effective, non-toxic amount of a compound of general formula I. The invention encompasses a method of treating or preventing asthma and/or chronic obstructive pulmonary disease (COPD) in a mammal.

Preferred features of each aspect of the invention apply to each other aspect of the invention, mutatis mutandis.

Figure 2:
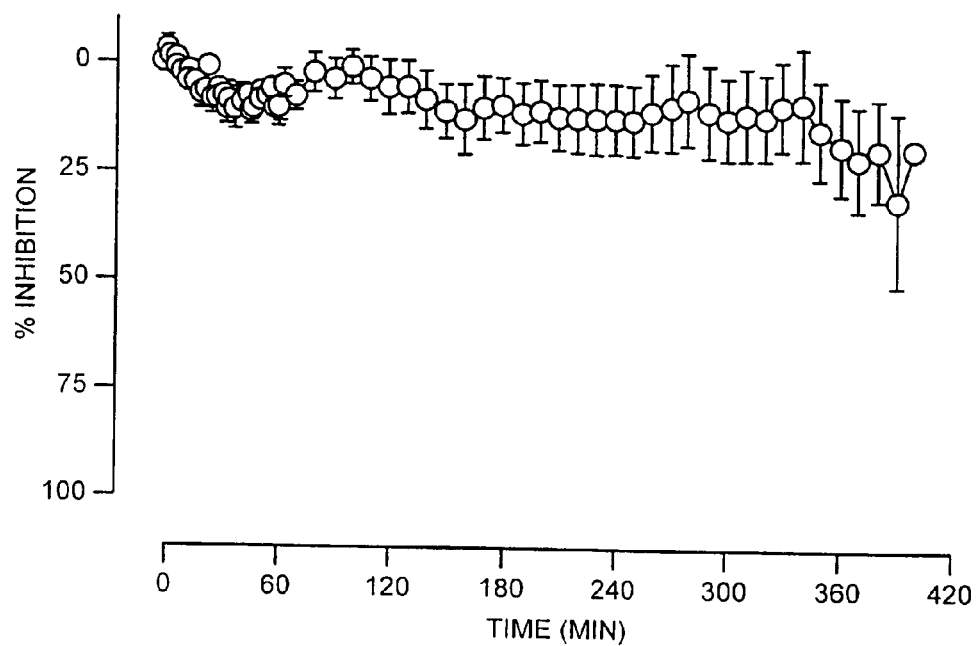
Figure 3:
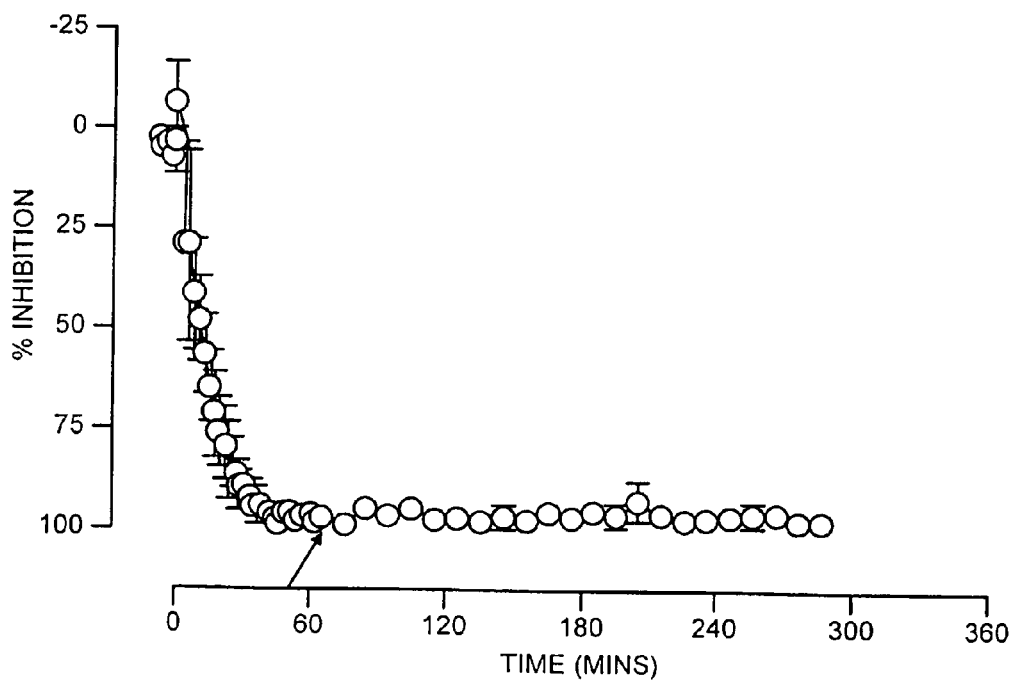
Figure 4:
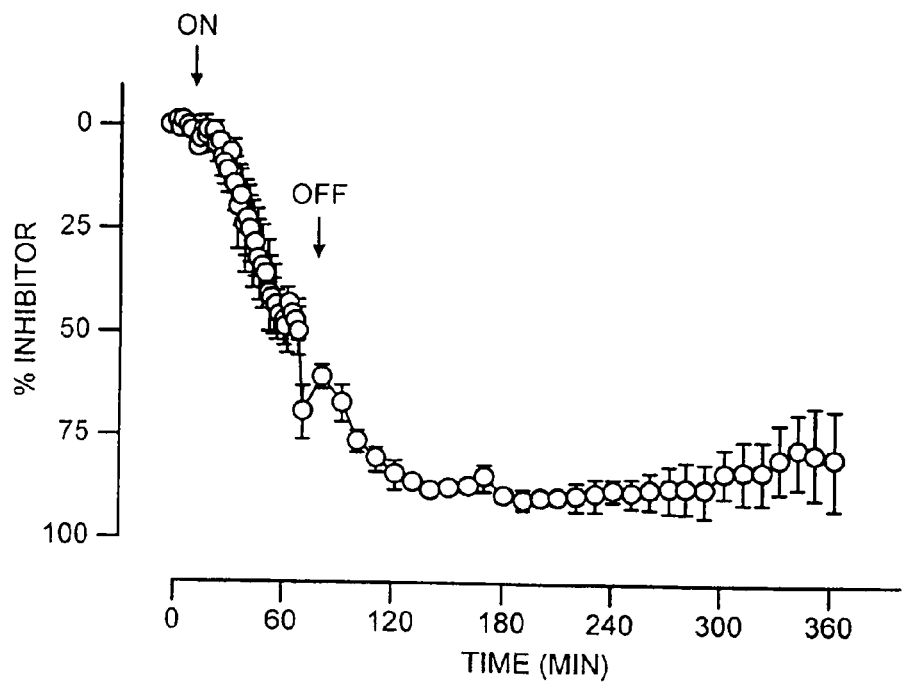
Figure 5:
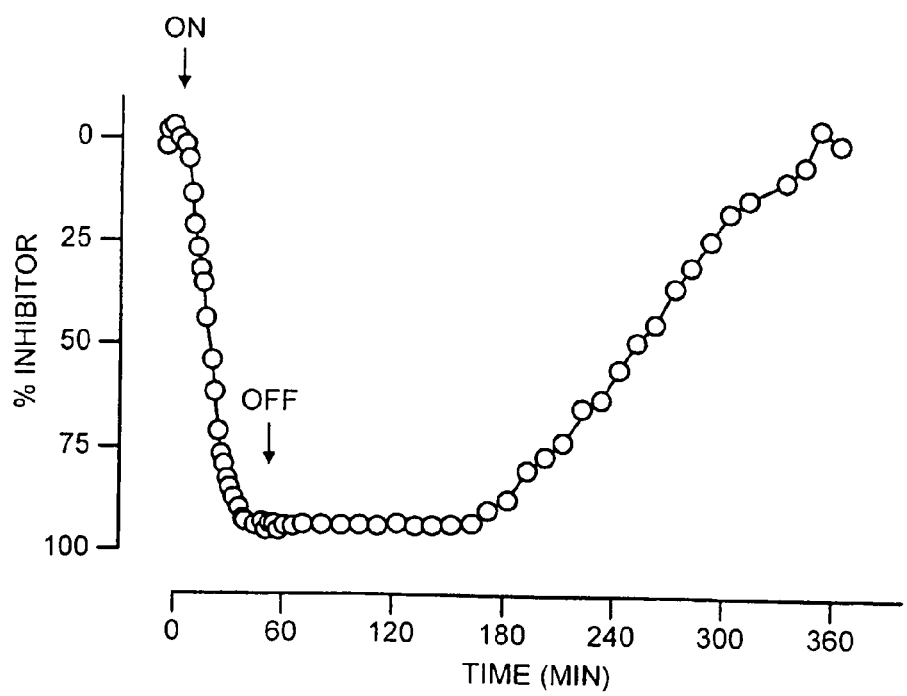
Figure 6:
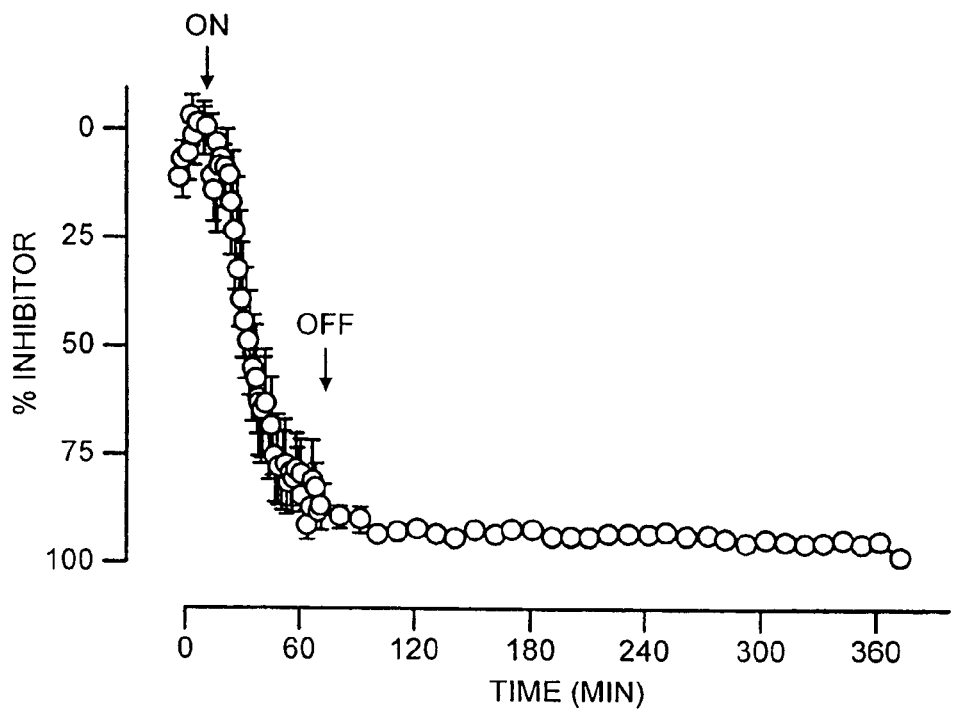
Figure 7:
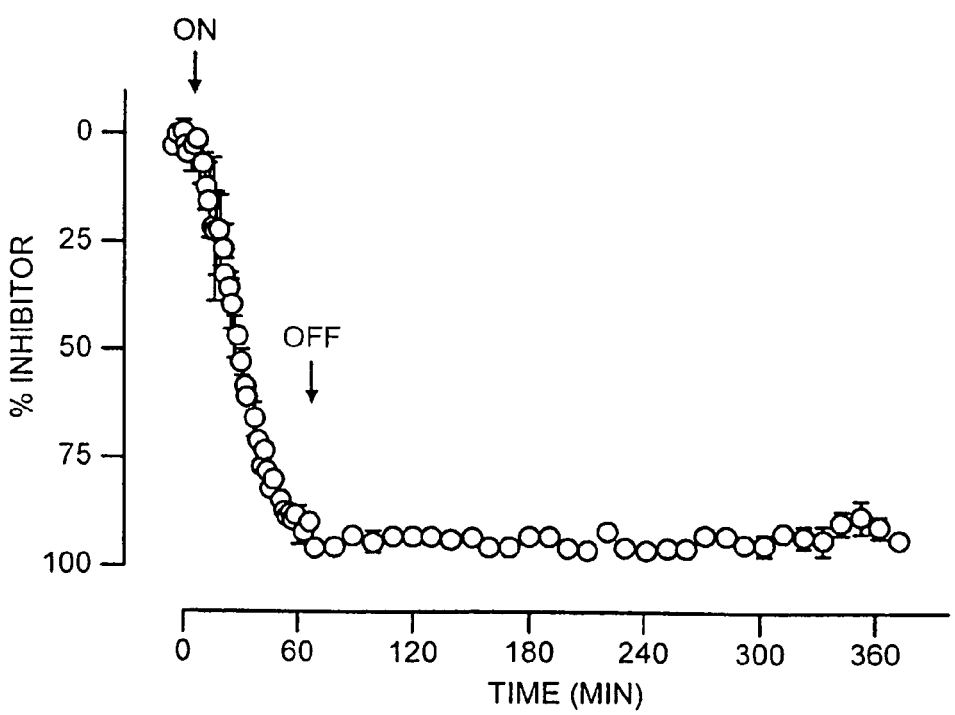
Figure 8:
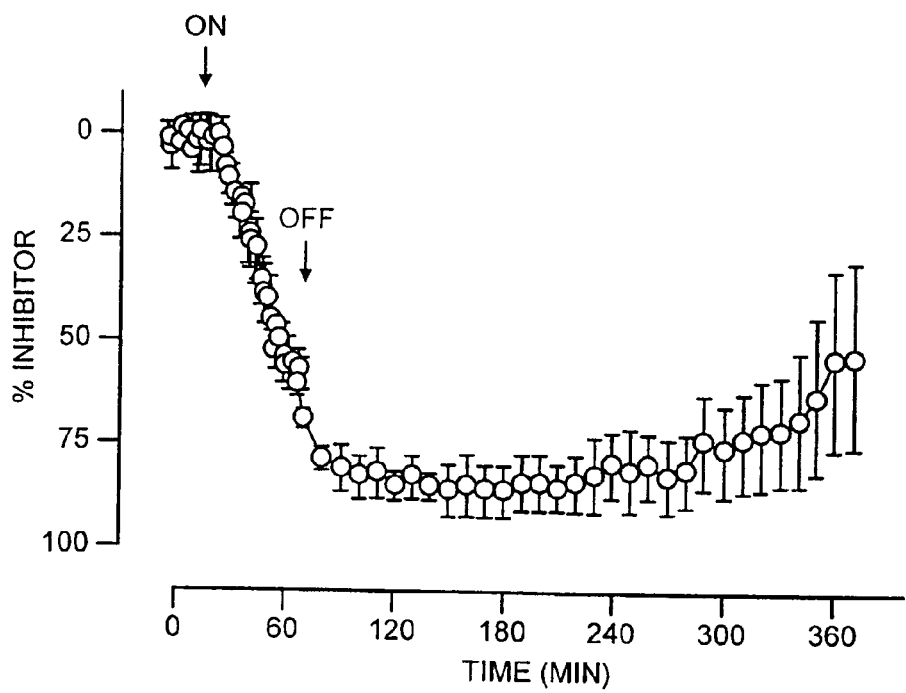
Figure 9:
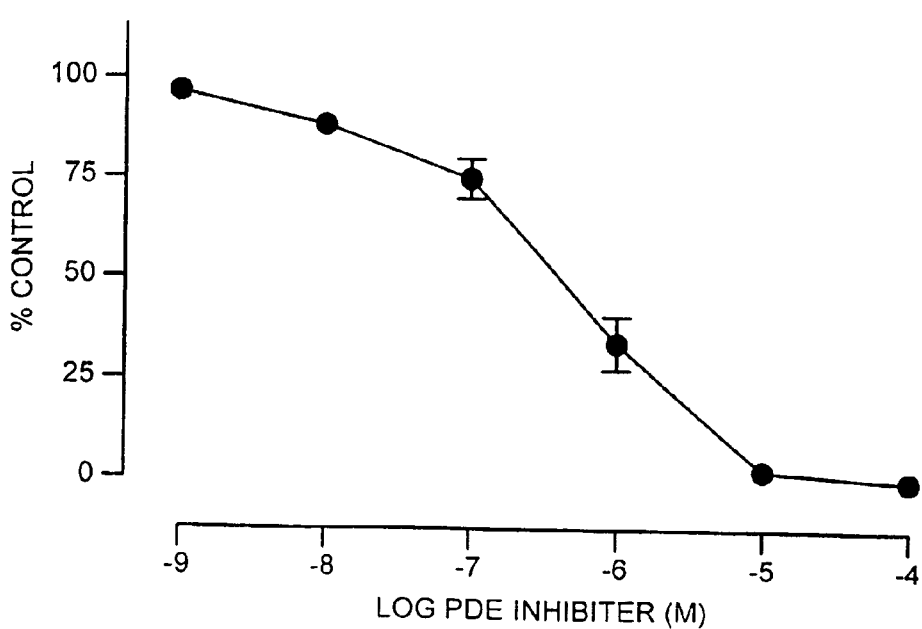

FIG. 1, referred to in Preparations 1 to 4 below, shows the route by which the compounds in Preparations 1 to 4 were synthesised;

FIG. 2, referred to in Example A below, is a graph showing the effect of DMSO on cholinergic contractile response in superfused guinea pig trachea, wherein "n" is the number of experiments;

FIG. 3, referred to in Example A below, is a graph showing the effect of 10 μM of the compound of Example 1 of the present invention on contraction of guinea pig trachea to electrical field stimulation over time (n=3), wherein the arrow denotes commencement of washout period;

FIG. 4, referred to in Example A below, is a graph showing the effect of 10 μM of the compound of Example 9 on contraction of guinea pig trachea to electrical field stimulation over time (n=3);

FIG. 5, referred to in Example A below, is a graph showing the effect of 10 μM of the compound of Example 10 on contraction of guinea pig trachea to electrical field stimulation over time (n=3), FIG. 6, referred to in Example A below, is a graph showing the effect of 10 μM of the compound of Example 11 on contraction of guinea pig trachea to electrical field stimulation over time (n=3);

FIG. 7, referred to in Example A below, is a graph showing the effect of 10 μM of the compound of Example 13 on contraction of guinea pig trachea to electrical field stimulation over time (n=3);

FIG. 8, referred to in Example A below, is a graph showing the effect of 10 μM of the compound of Example 8 on contraction of guinea pig trachea to electrical field stimulation over time (n=3);

FIG. 9 referred to in Example B below, is a graph showing the effect of the compound of Example 1 of the present invention against proliferation of human mononuclear cells stimulated by PHA, wherein each point represents the mean of six experiments, and vertical lines represent standard error of the mean.

PREPARATION 1

Synthesis of 2-Chloro-6,7-dihydro-9,10-Dimethoxy-4H-pyrimido[6,1-a]isoquinolin-4-one (Shown as (1) in FIG. 1)

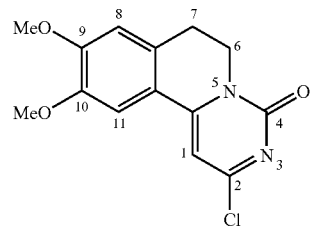

A mixture of 1-(3,4-dimethoxyphenyl) barbituric acid (70 g, 0.24 mol), prepared according to the method described in B. Lal et al. *J. Med. Chem.* 27 1470-1480 (1984), and phosphorus oxychloride (300 ml, 3.22 mol) was refluxed for 2.5 h. The excess phosphorous oxychloride was removed by distillation (20 mmHg) on warming. After cooling the residue was slurried in dioxan (100 ml) and cautiously added to a vigorously stirred ice/water solution (1 l). Chloroform (1 l) was added and the resulting mixture was basified with 30% sodium hydroxide solution. The organic layer was separated and the aqueous phase further extracted with chloroform (2×750 ml). The combined organic extracts were washed with water (1.5 l), dried over magnesium sulphate and concentrated in vacuo to leave a gummy material (90 g). This was stirred in methanol for a few minutes, filtered and washed with methanol (200 ml), diethyl ether (2×200 ml) and dried in vacuo at 40° C. to yield the title compound as a yellow/orange solid. 47 g, 62%

(300 MHz, CDCl$_3$) 2.96 (2H, t, C$_{(7)}$ H$_2$); 3.96 (6H, s, 2×OCH$_3$; 4.20 (2H, t, C$_{(6)}$ H$_2$); 6.61 (1H, s, C$_{(1)}$ H); 6.76 (1H, s, Ar—H); 7.10 (1H, s, Ar—H).

PREPARATION 2

9,10-Dimethoxy-2-(2,4,6-trimethylphenylimino)-3,4,6,7-tetrahydro-2H-pyrimido[6,1-a]isoquinolin-4-one (Shown as (2) in FIG. 1)

2-Chloro-9,10-dimethoxy-6,7-dihydro-4H-pyrimido[6,1-a]isoquinolin-4-one, prepared according to Preparation 1, (38.5 g, 0.13 mol) and 2,4,6-trimethylaniline (52.7 g, 0.39 mol) in propan-2-ol (3 l) was stirred and heated at reflux, under nitrogen, for 24 h. After cooling to room temperature, the solution was evaporated in vacuo and the residue was purified by column chromatography on silica gel, eluting with CH$_2$Cl$_2$/MeOH, initially 98:2, changing to 96:4 once the product began to elute from the column. The title compound was obtained with a slight impurity, (just above the product on tlc). Yield 34.6 g, 67%.

PREPARATION 3

9,10-Dimethoxy-2-(2,4,6-trimethylphenylimino)-3-(2-N-phthalimidoethyl)-3,4,6,7-tetrahydro-2H-pyrimido[6,1-a]isoquinolin-4-one (Shown as (3) in FIG. 1)

A mixture of 9,10-Dimethoxy-2-(2,4,6-trimethylphenylimino)-3,4,6,7-tetrahydro-2H-pyrimido[6,1-a]isoquinolin-4-one (which was prepared according to Preparation 2) (60.0 g, 0.153 mol), potassium carbonate (191 g, 1.38 mol), sodium iodide (137 g, 0.92 mol) and N-(2-bromoethyl)phthalimide (234 g, 0.92 mol) in 2-butanone (1500 ml) was stirred and heated at reflux, under nitrogen, for 4 days. After cooling to room temperature the mixture was filtered and the filtrate was evaporated in vacuo. The residue was treated with methanol (1000 ml) and the solid filtered off, washed with methanol and recrystallised from ethyl acetate to obtain the title compound as a pale yellow solid in yield 40.0 g, 46%. Evaporation of the mother liquor and column chromatography of the residue on silica gel (CH$_2$Cl$_2$/MeOH 95:5) provided further product 11.7 g, 13.5%.

PREPARATION 4

9,10-Dimethoxy-2-(2,4,6-trimethylphenylimino)-3-(2-aminoethyl)-3,4,6,7-tetrahydro-2H-pyrimido[6,1-a]isoquinolin-4-one (Shown as (4) in FIG. 1)

A mixture of 9,10-Dimethoxy-2-(2,4,6-trimethylphenylimino)-3-(2-N-phthalimidoethyl)-3,4,6,7-tetrahydro-2H-pyrimido[6,1-a]isoquinolin-4-one (22.0 g, 0.039 mol), prepared according to Preparation 3, and hydrazine hydrate (11.3 g, 0.195 mol) in chloroform (300 ml) and ethanol (460 ml) was stirred at room temperature, under nitrogen, for 18 h. Further hydrazine hydrate (2.9 g, 0.05 mol) was added and the mixture was stirred a further 4 h. After cooling in ice/water, the solid was removed by filtration and the filtrate evaporated in vacuo. The residue was dissolved in dichloromethane and the insoluble material was removed by filtration. The filtrate was dried (MgSO$_4$) and evaporated in vacuo to afford the title compound as a yellow foam in yield 16.2 g, 96%.

EXAMPLE 1

9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one

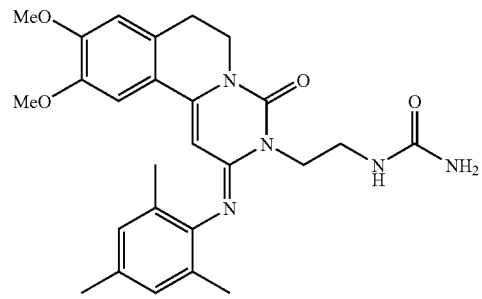

Sodium cyanate (6.0 g, 0.092 mol) in water (100 ml) was added dropwise to a stirred solution of 9,10-Dimethoxy-2-(2,4,6-trimethylphenylimino)-3-(1-aminoethyl)-3,4,6,7-tetrahydro-2H-pyrimido[6,1-a]isoquinolin-4-one, prepared according to Preparation 4 above (20.0 g, 0.046 mol) in water (600 ml) and 1N HCl (92 ml) at 80° C. After stirring for 2 h at 80° C. the mixture was cooled in an ice-bath and basified with 2N NaOH. The mixture was extracted with dichloromethane (3×200 ml) and the combined extract was dried (MgSO$_4$) and evaporated in vacuo. The resulting yellow foam was purified by column chromatography on silica gel eluting with CH$_2$Cl$_2$/MeOH (97:3) and triturated with ether to obtain the title compound as a yellow solid, 11.9 g, 54%.

| M.p.: | 234-236° C. | |
|---|---|---|
| m/z: | C$_{26}$H$_{31}$N$_5$O$_4$ requires M = 477 found (M + 1) = 478 | |
| HPLC: | Area (%) | 99.50 |
| | Column | ODS (150 × 4.6 mm) |
| | MP | pH 3 KH$_2$PO$_4$/CH$_3$CN (60/40) |
| | FR (ml/min) | 1.0 |
| | RT (min) | 9.25 |
| | Detection | 250 nm |

$^1$H NMR (300 MHz, CDCl$_3$): δ1.92 (1H, br s, NH), 2.06 (6H, s, 2×CH$_3$), 2.29 (3H, s, CH$_3$), 2.92 (2H, t, CH$_2$), 3.53 (2H, m, CH$_2$), 3.77 (3H, s, OCH$_3$), 3.91 (3H, s, OCH$_3$), 4.05

(2H, t, $CH_2$), 4.40 (2H, t, $CH_2$), 5.35 (2H, br s, $NH_2$), 5.45 (1H, s, C=CH), 6.68 (1H, s, ArH), 6.70 (1H, s, ArH), 6.89 (2H, s, 2×ArH).

EXAMPLE 2

9,10-Dimethoxy-2-(2,4,6-trimethylphenylimino)-3-[N—(N'-isopropylcarbamoyl)-2-aminoethyl]-3,4,6,7-tetrahydro-2H-pyrimido[6,1-a]isoquinolin-4-one

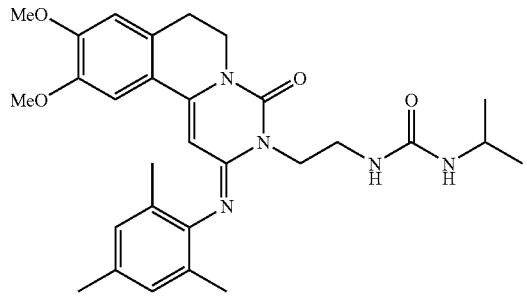

Isopropylisocyanate (0.15 g, 1.77 mmol) was added dropwise to a stirred solution of 9,1-Dimethoxy-2-(2,4,6-trimethylphenylimino)-3-(2-aminoethyl)-3,4,6,7-tetrahydro-2H-pyrimido[6,1-a]isoquinolin-4-one (prepared according to Preparation 4 above) (0.7 g, 1.61 mmol) in toluene (6 ml) at room temperature, under nitrogen. After 2 h the solution was evaporated in vacuo and the residue was purified by column chromatography on silica gel ($CH_2Cl_2$/MeOH, 97:3) and triturated with ether to obtain an off-white solid, 0.42 g, 50%.

| M.p.: | 181-182° C. |  |
|---|---|---|
| m/z: | $C_{29}H_{37}N_5O_4$ requires M = 519 found (M + 1) = 520 | |
| HPLC: | Area (%) | 94.99 |
| | Column | ODS (150 × 4.6 mm) |
| | MP | pH 3 $KH_2PO_4$/$CH_3CN$ (40/60) |
| | FR (ml/min) | 1.0 |
| | RT (min) | 7.985 |
| | Detection | 250 nm |

$^1$H NMR (300 MHz, $CDCl_3$): δ 0.89 (6H, d, 2×$CH_3$), 2.05 (6H, s, 2×$CH_3$), 2.29 (3H, s, $CH_3$), 1.94 (1H, br s, NH), 2.90 (2H, t, $CH_2$), 3.49 (2H, m, $CH_2$), 3.77 (3H, s, $OCH_3$), 3.91 (3H, s, $OCH_3$), 4.05 (2H, t, $CH_2$), 4.37 (2H, t, $CH_2$), 5.02 (1H, br s, NH), 5.46 (1H, s, C=CH), 6.67 (1H, s, ArH), 6.69 (1H, s, ArH), 6.87 (2H, s, 2×ArH).

EXAMPLE 3

9,10-Dimethoxy-2-(2,4,6-trimethylphenylimino)-3-[N-[1-(N'-methyl-2-nitroethenamine)]-2-aminoethyl]-3,4,6,7-tetrahydro-2H-pyrimido[1,6-a]-isoquinolin-4-one

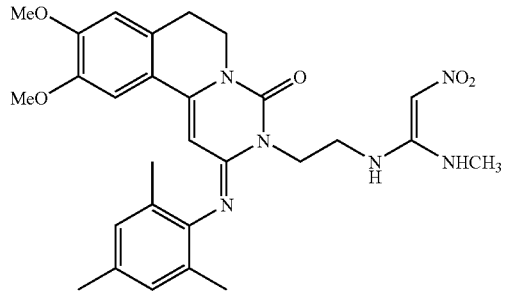

A mixture of 9,10-Dimethoxy-2-(2,4,6-trimethylphenylimino)-3-(2-aminoethyl)-3,4,6,7-tetrahydro-2H-pyrimido[6,1-a]isoquinolin-4-one, prepared according to Preparation 4 above (0.8 g, 1.84 mmol) and N-methyl-1-(methylthio)-2-nitroethenamine (0.30 g, 2.03 mmol) in toluene (20 ml) was stirred and heated at reflux, under nitrogen, for 2 h. After cooling to room temperature the solvent was evaporated in vacuo and the residue was purified by column chromatography on silica gel ($CH_2Cl_2$/MeOH, 97:3). The title compound was obtained as a yellow foam in yield 0.61 g, 62%, which on triturating with ether yielded a yellow solid 0.40 g, 41%.

| M.p.: | 126-130° C. |  |
|---|---|---|
| m/z: | $C_{28}H_{34}N_6O_5$ requires M = 534 found (M + 1) = 535 | |
| HPLC: | Area (%) | 98.98 |
| | Column | ODS (150 × 4.6 mm) |
| | MP | pH 4 $KH_2PO_4$/$CH_3CN$ (45/55) |
| | FR (ml/min) | 1.0 |
| | RT (min) | 6.635 |
| | Detection | 250 nm |

$^1$H NMR (300 MHz, $CDCl_3$): δ 2.07 (6H, s, 2×$CH_3$), 2.29 (3H, s, $CH_3$), 2.45 (3H, d, $NHCH_3$), 2.92 (2H, t, $CH_2$), 3.65 (2H, m, $CH_2$), 3.77 (3H, s, $OCH_3$), 3.90 (3H, s, $OCH_3$), 4.08 (2H, t, $CH_2$), 4.32 (2H, m, $CH_2$), 5.46 (1H, s, =CH), 6.51 (1H, s, $CHNO_2$), 6.70 (2H, s, 2×ArH), 6.90 (2H, s, 2×ArH), 8.78 (1H, m, NH), 10.35 (1H, m, NH).

EXAMPLE 4

9,10-Dimethoxy-2-(2,4,6-trimethylphenylimino)-3-[N-[1-(N'-isopropyl-2-nitroethenamine)]-2-aminoethyl]-3,4,6,7-tetrahydro-2H-pyrimido[6,1-a]-isoquinolin-4-one 1,1-Bis(methylthio)-2-nitroethylene (5.3 g, 32.2 mmol) and 9,10-Dimethoxy-2-(2,4,6-trimethylphenylimino)-3-(2-aminoethyl)-3,4,6,7-tetrahydro-2H-pyrimido[6,1-a]isoquinolin-4-one, prepared according to Preparation 4 above (1.4 g, 3.22 mmol) in toluene (20 ml) was stirred and heated at reflux, under nitrogen, for 2 h. After cooling to room temperature the solvent was evaporated in vacuo and the residue was purified by column chromatography on silica gel ($CH_2Cl_2$/MeOH, 99:1). This yielded intermediate compound (shown as compound A below) as an oil which became a light beige solid upon trituration with ether. Yield 0.95 g, 53%.

Isopropylamine (5 ml) was added to a stirred solution of (A) (0.7 g, 1.27 mmol) in dichloromethane (10 ml) and heated at reflux, under nitrogen, for 20 h. After cooling, the solution was evaporated in vacuo and the residue was purified by column chromatography on silica gel ($CH_2Cl_2$/MeOH, 98:2). The title compound (shown as compound B below) was obtained as a foam in yield 0.64 g, 89%. This became a pale yellow solid (0.38 g) upon trituration with ether.

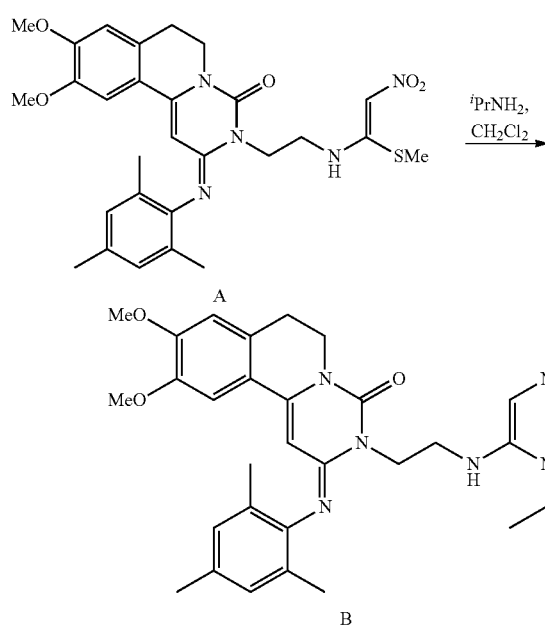

| M.p.: | 144-146° C. |
|---|---|
| m/z: | $C_{30}H_{38}N_6O_5$ requires M = 562 found (M + 1) = 563 |
| HPLC: | Area (%) 97.57 |
| | Column ODS (150 × 4.6 mm) |
| | MP pH 4 $KH_2PO_4/CH_3CN$ (40/60) |
| | FR (ml/min) 1.0 |
| | RT (min) 9.028 |
| | Detection 250 nm |

$^1$H NMR (300 MHz, $CDCl_3$): δ 0.87 (6H, d, $CH(CH_3)_2$), 2.05 (6H, s, 2×$CH_3$), 2.29 (3H, s, $CH_3$), 2.93 (2H, m, $CH_2$), 3.48 (1H, m $CH(CH_3)_2$), 3.68 (2H, m, $CH_2$), 3.78 (3H, s, $OCH_3$), 3.91 (3H, s, $OCH_3$), 4.09 (2H, t, $CH_2$), 4.34 (2H, m, $CH_2$), 5.48 (1H, s, C=CH), 6.68 (1H, s, $CHNO_2$), 6.69 (2H, s, 2×ArH), 6.90 (2H, s, 2×ArH), 7.04 (1H, d, NH), 10.75 (1H, m, NH).

EXAMPLE 5

9,10-Dimethoxy-2-(2,4,6-trimethylphenylimino)-3-[N-[1-(N',N'-dimethyl-2-nitroethenamine)]-2-aminoethyl]-3,4,6,7-tetrahydro-2H-pyrimido[6,1-a]-isoquinolin-4-one

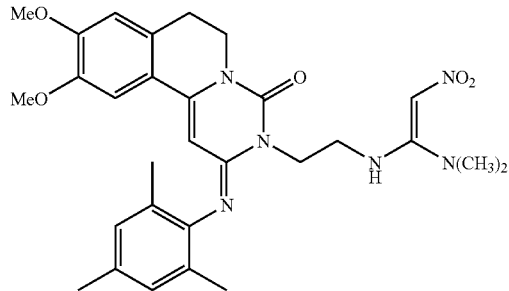

A solution of compound A shown in Example 4 above (1.0 g, 1.81 mmol) and dimethylamine (33% in EtOH, 5.0 ml, 28 mmol) in dichloromethane (10 ml) was stirred at 35° C., under nitrogen, for 18 h. The solution was then evaporated in vacuo and the residue was purified by column chromatography on silica gel ($CH_2Cl_2$/MeOH, 97:3) to obtain the title compound as a yellow foam in yield 0.73 g, 73%. This became a pale yellow solid (0.60 g) upon trituration with ether.

| M.p.: | 187-189° C. |
|---|---|
| m/z: | $C_{29}H_{36}N_6O_5$ requires M = 548 found (M + 1) = 549 |
| HPLC: | Area (%) 97.89 |
| | Column ODS (150 × 4.6 mm) |
| | MP pH 4 $KH_2PO_4/CH_3CN$ (45/55) |
| | FR (ml/min) 1.0 |
| | RT (min) 6.768 |
| | Detection 250 nm |

$^1$H NMR (300 MHz, $CDCl_3$): δ 2.02 (6H, s, 2×$CH_3$), 2.28 (3H, s, $CH_3$), 2.95 (2H, m, $CH_2$), 2.95 (6H, s, $N(CH_3)_2$), 3.78 (3H, s, $OCH_3$), 3.81 (2H, t, $CH_2$), 3.90 (3H, s, $OCH_3$), 4.05 (2H, t, $CH_2$), 4.55 (2H, t, $CH_2$), 5.43 (1H, s, C=CH), 6.47 (1H, s, ArH), 6.67 (1H, s, $CHNO_2$), 6.70 (1H, s, ArH), 6.89 (2H, s, 2×ArH), 9.35 (1H, m, NH).

EXAMPLE 6

9,10-Dimethoxy-2-(2,4,6-trimethylphenylimino)-3-[N—(N'-phenylcarbamoyl)-2-aminoethyl]-3,4,6,7-tetrahydro-2H-pyrimido[6,1-a]isoquinolin-2-one

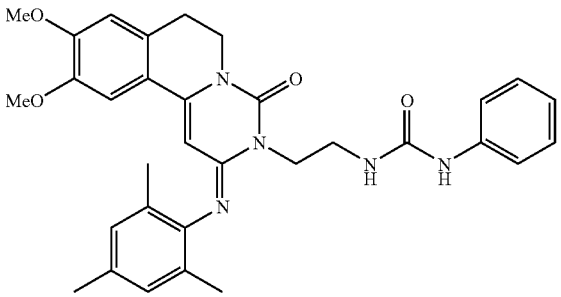

Phenylisocyanate (0.16 g, 1.38 mmol) was added dropwise to a stirred solution of 9,10-Dimethoxy-2-(2,4,6-trimethylphenylimino)-3-(2-aminoethyl)-3,4,6,7-tetrahydro-2H-pyrimido[6,1-a]isoquinolin-4-one, prepared according to Preparation 4 above (0.6 g, 1.38 mmol) in toluene (5 ml) at room temperature, under nitrogen. After 1 h the solvent was evaporated in vacuo and the residue was purified by column chromatography on silica gel ($CH_2Cl_2$/MeOH, 95:5). After trituration with ether the title compound was obtained as a pale yellow solid 0.61 g, 80%.

| M.p.: | 116-118° C. |
|---|---|
| m/z: | $C_{32}H_{33}N_5O_4$ requires M = 553 found (M + 1) = 554 |
| HPLC: | Area (%) 98.80 |
| | Column ODS (150 × 4.6 mm) |
| | MP 0.02M $KH_2PO_4/CH_3CN$ (42/58) |
| | FR (ml/min) 0.8 |
| | RT (min) 10.622 |
| | Detection 254 nm |

$^1$H NMR (300 MHz, $CDCl_3$): δ 2.05 (6H, s, 2×$CH_3$), 2.30 (3H, s, $CH_3$), 2.92 (2H, t, $CH_2$), 3.67 (2H, m, $CH_2$), 3.78 (3H, s, $OCH_3$), 3.91 (3H, s, $OCH_3$), 4.06 (2H, t, $CH_2$), 4.47 (2H, t, $CH_2$), 5.51 (1H, s, C=CH), 5.60 (1H, s br, NH), 6.69 (1H, s,

ArH), 6.72 (1H, s, ArH), 6.89 (2H, s, 2×ArH), 6.90-7.23 (5H, m, 5×ArH), 7.62 (1H, br s, NH).

EXAMPLE 7

9,10-Dimethoxy-3-[2-guanidinoethyl]-2-(2,4,6-trimethylphenylimino)-3,4,6,7-tetrahydro-2H-pyrimido[6,1-a]isoquinolin-4-one

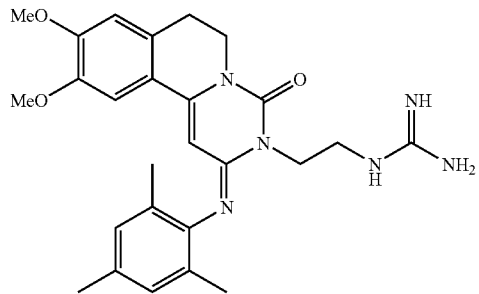

1,3-Di-(tert-butoxycarbonyl)thiourea (1)

Sodium hydride (60% in oil, 4.7 g, 0.117 mol) was washed with petroleum ether to remove the oil, then added in portions to a stirred solution of thiourea (2.0 g, 0.026 mol) in tetrahydrofuran (400 ml) at 0° C., under nitrogen. The mixture was stirred for 5 minutes at 0° C. then warmed to room temperature for 10 minutes. After re-cooling to 0° C., di-tert-butyl dicarbonate (16.1 g, 0.0585 mol) in tetrahydrofuran (100 ml) was added dropwise and the mixture was stirred for 30 minutes at 0° C. After a further 2 h at room temperature the reaction was quenched by dropwise addition of saturated sodium bicarbonate (40 ml) and poured into water (1 l). The solution was extracted with ethyl acetate (3×200 ml) and the combined extract washed with brine, dried (MgSO₄) and evaporated in vacuo. The residual solid was triturated with petroleum ether, removed by filtration and dried in vacuo. The title compound (4.3 g, 60%) was obtained as an off-white solid. M.p. 124-127° C.

3-[N—(N',N'-Di-tert-butoxycarbonyl)-2-guanidinoethyl]-9,10-dimethoxy-2-(2,4,6-trimethylphenylimino)-3,4,6,7-tetrahydro-2H-pyrimido[6,1-a]isoquinolin-4-one (3)

1-Methyl-2-chloropyridinium iodide (0.77 g, 3.03 mmol) in N,N-dimethylformamide (4 ml) was added dropwise to a stirred mixture of N,N'-di-(tert-butoxycarbonyl)thiourea (0.84 g, 3.03 mmol), 3-(2-aminoethyl)-9,10-dimethoxy-2-(2,4,6-trimethylphenylimino)-3,4,6,7-tetrahydro-2H-pyrimido[6,1-a]isoquinolin-4-one (2) (1.1 g, 2.53 mmol) and triethylamine (0.56 g, 5.57 mmol) in N,N-dimethylformamide (8 ml). After 18 h the reaction was quenched by addition of water (40 ml) and extracted with ethyl acetate (3×25 ml). The combined extract was washed with brine, dried (MgSO₄) and evaporated in vacuo. The residual oil was purified by column chromatography on silica gel (petroleum ether/ethyl acetate, 2:1) to obtain the title compound (1.05 g, 61%) as a yellow foam.

M/z [ES]+ 677.

9,10-Dimethoxy-3-[2-guanidinoethyl]-2-(2,4,6-trimethylphenylimino)-3,4,6,7-tetrahydro-2H-pyrimido[6,1-a]isoquinolin-4-one Trifluoroacetic acid (0.35 g, 3.1 mmol was added to a stirred solution of 3 (0.95 g, 1.4 mmol) in dichloromethane (5 ml) at room temperature. After 3 h further trifluoroacetic acid (0.35 g) was added and the mixture was stirred for an additional 16 h. The solvent was then evaporated in vacuo and the residue was treated with dichloromethane (20 ml) and basified to pH 10 with saturated sodium bicarbonate. The organic phase was separated, dried (MgSO₄) and evaporated in vacuo. The residual oil was purified by column chromatography on silica gel (CH₂Cl₂/MeOH, 98:2→90:10) to obtain the title compound, after trituration with diethyl ether, as an off-white solid, 0.27 g, 40%.

| M.p.: | 226-228° C. |
| --- | --- |
| M/z: | C₂₆H₃₂N₆O₃ requires M = 476, found m/z [ES]+ = 477 |
| HPLC: | |
| Area (%) | 98.73 |
| Column | ODS LUNA 3uC18(2) (100 × 4.6 mm) |
| MP | 0.1% CF₃CO₂H/CH₃CN (gradient 90% aq → 25% aq over 25 min) |
| RT (min) | 11.413 |
| FR (ml/min) | 0.8 |
| Detection | 250 nm |

¹H NMR (250 MHz, CDCl₃, 70° C.): δ 2.03 (6H, s, 2×CH₃), 2.26 (3H, s, CH₃), 2.95 (2H, t, CH₃), 3.57 (2H, m, CH₂), 3.67 (3H, s, OCH₃), 3.85 (3H, s, OCH₃), 3.98 (2H, t, CH₂), 4.33 (2H, t, CH₂), 5.40 (1H, s, C=CH), 6.73 (1H, s, ArH), 6.91 (2H, s, 2×ArH), 6.98 (1H, s, ArH), 7.25 (2H, br s, NH₂), 7.73 (1H, m, NH).

The ¹H NMR was run at 70° C. to obtain better resolution because some of the signals were poorly resolved at room temperature.

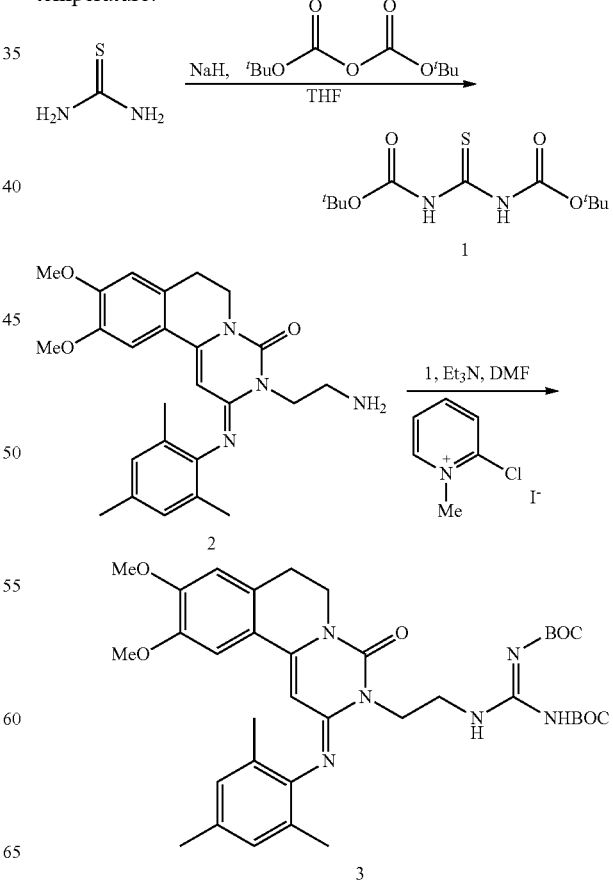

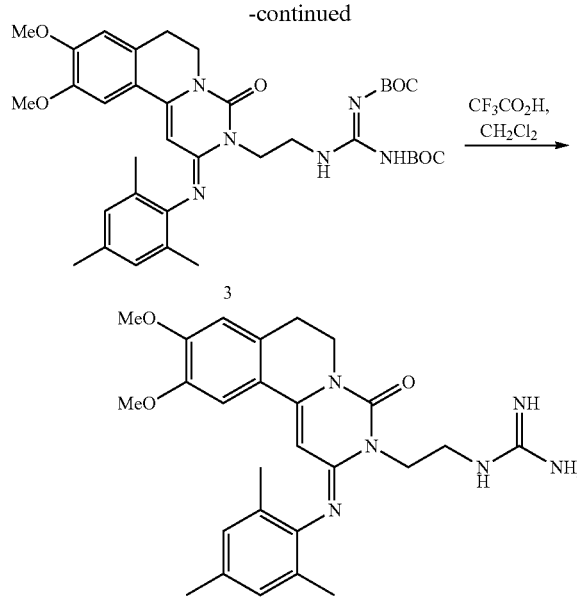

EXAMPLE 8

9,10-Dimethoxy-3-[N—(N'-nitro)-2-guanidinoethyl]-2-(2,4,6-trimethylphenylimino)-3,4,6,7-tetrahydro-2H-pyrimido[6,1-a]isoquinolin-4-one

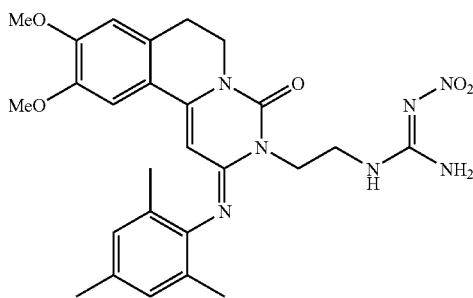

2-Methyl-1-nitro-2-isothiourea (1)

S-Methylisothiouronium sulphate (3.0 g, 10.8 mmol) was added in portions to a stirred mixture of fuming nitric acid (3 ml) and concentrated sulphuric acid (9 ml) at −10 to +5° C. After stirring for a further 30 min at 5° C. the solution was poured onto ice (120 g) with stirring. The white solid was removed by filtration, washed with water and dried in vacuo to obtain 2-methyl-1-nitro-2-isothiourea (2.0 g, 69%).

9,10-Dimethoxy-3-[N—(N'-nitro)-2-guanidinoethyl]-2-(2,4,6-trimethylphenylimino)-3,4,6,7-tetrahydro-2H-pyrimido[6,1-a]isoquinolin-4-one 2-Methyl-1-nitro-2-isothiourea (0.405 g, 3.0 mmol) was added to a stirred solution of 3-(2-aminoethyl)-9,10-dimethoxy-2-(2,4,6-trimethylphenylimino)-3,4,6,7-tetrahydro-2H-pyrimido[6,1-a]isoquinolin-4-one (1.29 g, 3.0 mmol) in ethanol (12 ml) and heated to 70° C. for 30 min. The solvent was then evaporated in vacuo and the residue was purified by column chromatography on silica gel [CH$_2$Cl$_2$/MeOH, 97:3)] to obtain the title compound as a pale yellow solid (0.76 g, 49%).

| M.p.: | 253-256° C. |
| --- | --- |
| M/z: | C$_{26}$H$_{31}$N$_7$O$_5$ requires M = 521, found m/z [ES]+ = 522 |
| HPLC: | Area (%) 99.44 |
| | Column ODS LUNA 3uC18(2) (100 × 4.6 mm) |
| | MP 0.1% CF$_3$CO$_2$H/CH$_3$CN |
| | (gradient 90% aq → 25% aq over 25 min) |
| | RT (min) 16.842 |
| | FR (ml/min) 1.0 |
| | Detection 250 nm |

$^1$H NMR (250 MHz, d$_6$-DMSO, 70° C.): δ 2.02 (6H, s, 2×CH$_3$), 2.25 (3H, s, CH$_3$), 2.94 (2H, t, CH$_2$), 3.63 (2H, m, CH$_2$), 3.66 (3H, s, OCH$_3$), 3.84 (3H, s, OCH$_3$), 3.96 (2H, t, CH$_2$), 4.37 (2H, t, CH$_2$), 5.38 (1H, s, C═CH), 6.72 (1H, s, ArH), 6.88 (2H, s, 2×ArH), 6.96 (1H, s, ArH), 7.89 (1H, br s, NH).

The $^1$H NMR was run at 70° C. to obtain better resolution because some of the signals were poorly resolved at room temperature.

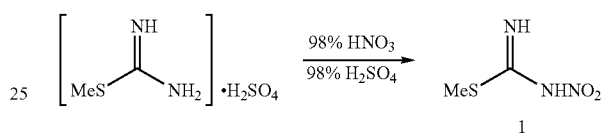

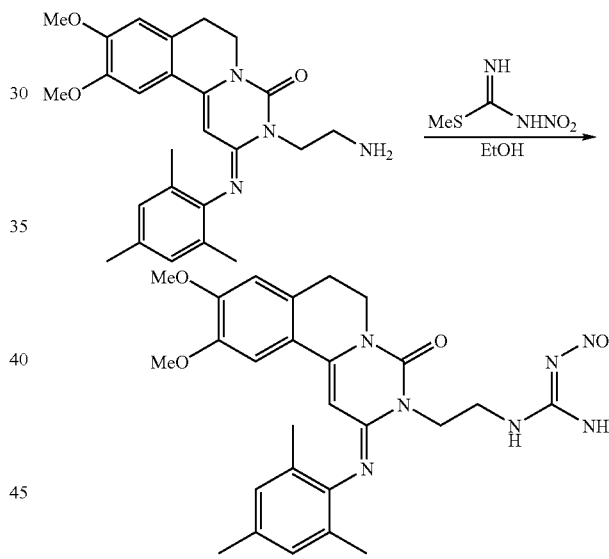

EXAMPLE 9

3-[N—(N'-Cyclohexylcarbamoyl)-2-aminoethyl]-9,10-dimethoxy-2-(2,4,6-trimethyl-phenylimino3,4,6,7-tetrahydro-2H-pyrimido[6,1-a]isoquinolin-4-one

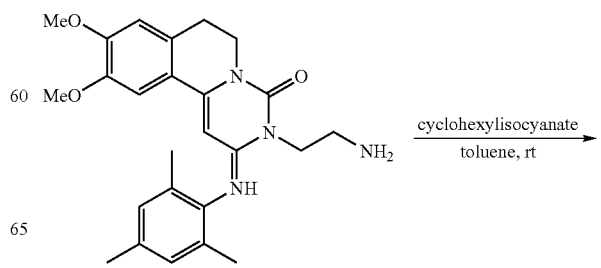

-continued

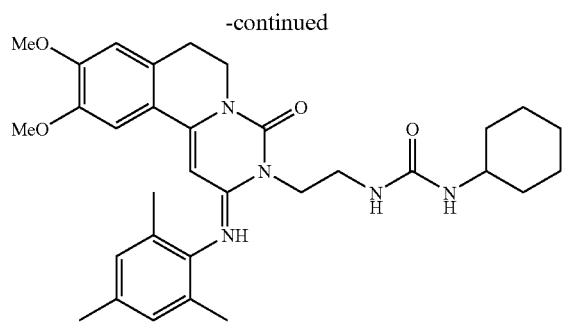

Cyclohexylisocyanate (0.38 g, 3.04 mmol) in toluene (2 ml) was added dropwise to a stirred solution of 3-(2-aminoethyl)-9,10-dimethoxy-2-(2,4,6-trimethylphenylimino)-3,4,6,7-tetrahydro-2H-pyrimido[6,1-a]isoquinolin-4-one (1.2 g, 2.76 mmol) in toluene (8 ml) at room temperature, under nitrogen. After stirring for 16 h the solution was evaporated in vacuo and the residue was purified by column chromatography on silica gel [dichloromethane/methanol (97:3)]. The product was triturated with ether to obtain the title compound (0.61 g, 40%) as a pale yellow solid.

| M.p.: | 120-122° C. |
| --- | --- |
| M/z: | $C_{32}H_{41}N_5O_4$ requires M = 559, found m/z [ES+] = 560 |
| HPLC: | Area (%) 98.59 |
| | Column ODS LUNA 3uC18(2) |
| | MP 0.1M $NH_4OAc/CH_3CN$ (40/60) |
| | RT (min) 9.145 |
| | FR (ml/min) 0.7 |
| | Detection 250 nm |

$^1$H NMR (300 MHz, $CDCl_3$): δ 0.7-1.8 (11H, m, cyclohexyl), 2.05 (6H, s, 2×$CH_3$), 2.27 (3H, s, $CH_3$), 2.93 (2H, t, $CH_2$), 3.49 (2H, m, $CH_2$), 3.78 (3H, s, $OCH_3$), 3.91 (3H, s, $OCH_3$), 4.05 (2H, t, $CH_2$), 4.37 (2H, t, $CH_2$), 5.49 (1H, s, C═CH), 5.80 (1H, br s, NH), 6.69 (1H, s, ArH), 6.70 (1H, s, ArH), 6.90 (2H, s, 2×ArH).

EXAMPLE 10

3-(N-Carbamoyl-2-aminoethyl)-9,10-dimethoxy-2-(2-methylphenylimino)-3,4,6,7-tetrahydro-2H-pyrimido[6,1-a]isoquinolin-4-one

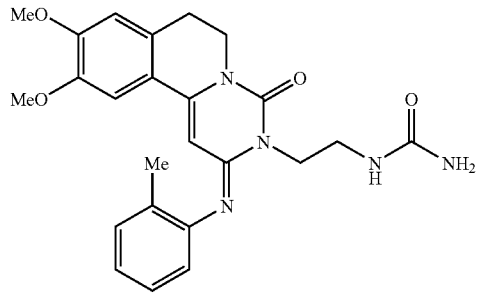

9,10-Dimethoxy-2-(2-methylphenylimino)-3,4,6,7-tetrahydro-2H-pyrimido[6,1-a]isoquinolin-4-one (1)

2-Methylaniline (5.44 ml, 51 mmol) and 2-chloro-9,10-dimethoxy-6,7-dihydro-4H-pyrimido[6,1-a]isoquinolin-4-one (5 g, 17 mmol) were suspended in propan-2-ol (400 ml) and heated at reflux, under nitrogen, for 24 h. After cooling to room temperature, the solution was concentrated in vacuo and the residue purified by flash column chromatography [dichloromethane/methanol (98:2-96:4)] to afford the title compound (6.2 g, quantitative yield) as a yellow/orange solid.

9,10-Dimethoxy-2-(2-methylphenylimino)-3-(N-phthalimidoethyl)-3,4,6,7-tetrahydro-2H-pyrimido[6,1-a]isoquinolin-4-one (2)

A mixture of isoquinoline 1 (6.2 g, 17 mmol), potassium carbonate (21.1 g, 153 mmol), sodium iodide (15.3 g, 102 mmol) and N-(2-bromoethyl)phthalimide (25.9 g, 102 mmol) in 2-butanone (170 ml) was stirred at reflux, under nitrogen, for 7 days. After cooling to room temperature, the mixture was filtered and the residue washed with methanol (150 ml). The filtrate was concentrated in vacuo and the resultant residue treated with methanol (100 ml) and the solid filtered off and washed with methanol. This solid Was washed with ether to give the title compound (2.67 g, 30%) as a pale yellow solid 3-(2-Aminoethyl)-9,10-dimethoxy-2-(2-methylphenylimino)-3,4,6,7-tetrahydro-2H-pyrimido[6,1-a]isoquinolin-4-one (3)

A mixture of phthalimide 2 (2.66 g, 4.96 mmol) and hydrazine monohydrate (1.24 g, 24.8 mmol) in chloroform (35 ml) and ethanol (60 ml) was stirred at room temperature, under nitrogen, for 18 h. Additional hydrazine hydrate (0.25 g, 5 mmol) was added and the mixture stirred for a further 5 h. After cooling to 0° C. in an ice/water bath, the solid was removed by filtration, the residue washed with a little cold chloroform and the filtrate concentrated in vacuo. This residue was taken up in dichloromethane and the insoluble material removed by filtration. The filtrate was dried ($MgSO_4$), filtered and concentrated in vacuo to afford the title compound (2.05 g, quantitative yield) as a yellow foam.

3-(N-Carbamoyl-2-aminoethyl)-9,10-dimethoxy-2-(2-methylphenylimino)-3,4,6,7-tetrahydro-2H-pyrimido[6,1-a]isoquinolin-4-one Sodium cyanate (0.64 g, 9.8 mmol) in water (13 ml) was added dropwise to a stirred solution of amine 3 (2 g, 4.9 mmol) in water (63 ml) and 1M HCl (9.8 ml) at 80° C. After stirring for 3 h at 80° C. the mixture was cooled and basified with 2M NaOH. The mixture was extracted with $CH_2Cl_2$ until no more product remained in the organic phase. The organic phases were combined, dried ($MgSO_4$), filtered and concentrated in vacuo. The residue was purified by column chromatography [dichloromethane/methanol (97:3)] and the product triturated with ether to afford the title compound (1.0 g, 45%) as a pale yellow solid.

| M.p.: | 236-238° C. |
| --- | --- |
| m/z: | $C_{24}H_{27}N_5O_4$ requires M = 449, found (M + 1) = 450 |
| HPLC: | Area 100% |
| | Column ODS LUNA (150 4.6 mm) |
| | MP pH 3 $KH_2PO_4/CH_3CN$ gradient 90% aq going to 50% over 25 mins |
| | FR 1.0 ml$min^{-1}$ |
| | RT 14.284 min |
| | Detection 250 nm |

$^1$H NMR (300 MHz; $d_6$-DMSO): δ 2.08 (3H, s, $CH_3$), 2.89 (2H, t, $CH_2$), 3.60 (3H, s, OMe), 3.79 (3H, s, OMe), 3.91 (2H, t, CH$_2$), 4.14 (2H, t, CH$_2$), 5.44 (2H, br s, NH$_2$), 5.64 (1H, s, vinylic H), 6.07 (1H, t, NH), 6.71 (1H, s, ArH), 6.73 (1H, d, ArH), 6.92 (1H, t, ArH), 6.95 (1H, s, ArH), 7.13 (1H, t, ArH), 7.19 (1H, d, ArH).
NB. The proton NMR spectrum above does not show the chemical shift for one CH$_2$ group as it is believed that this signal is obscured by the water signal present in the d$_6$-DMSO at 3.31-3.35.
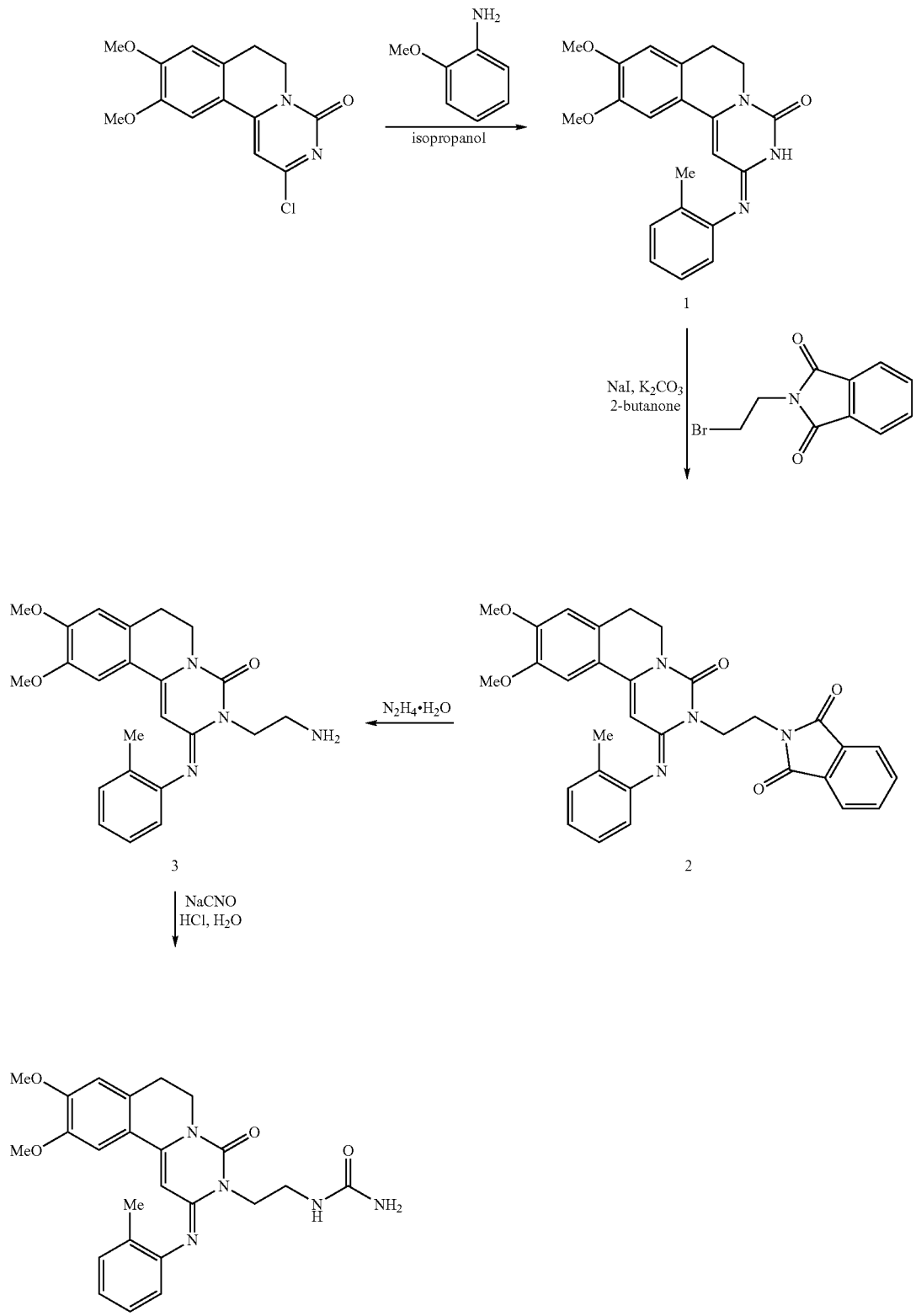

EXAMPLE 11

3-(N-Carbamoyl-2-aminoethyl)-2-(2,6-diisopropylphenylimino)-9,10-dimethoxy-3,4,6,7-tetrahydro-2H-pyrimido[6,1-a]isoquinolin-4-one

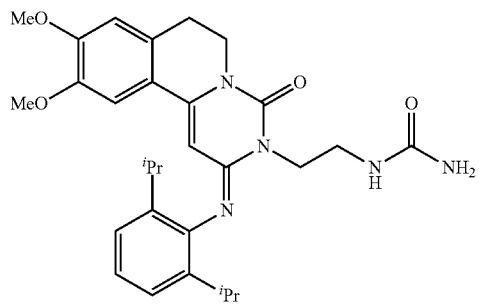

2-(2,6-Diisopropylphenylimino)-9,10-dimethoxy-3,4,6,7-tetrahydro-2H-pyrimido-[6,1-a]isoquinolin-4-one (1)

2,6-Diisopropylaniline (9.62 ml, 51 mmol) and 2-chloro-9,10-dimethoxy-6,7-dihydro-4H-pyrimido[6,1-a]isoquinolin-4-one (5 g, 17 mmol) were suspended in propan-2-ol (400 ml) and heated at reflux, under nitrogen, for 4 days. After cooling to room temperature, the solution was concentrated in vacuo and the residue purified by flash column chromatography [dichloromethane/methanol (98:2-96:4)] to afford the title compound (5.8 g, 79%) as a yellow/orange solid.

2-(2,6-Diisopropylphenylimino)-9,10-dimethoxy-3-(N-phthalimidoethyl)-3,4,6,7-tetrahydro-2H-pyrimido[6,1-a]isoquinolin-4-one (2)

A mixture of isoquinoline 1 (5.8 g, 13.4 mmol), potassium carbonate (16.7 g, 121 mmol), sodium iodide (12.1 g, 80 mmol) and N-(2-bromoethyl)phthalimide (25.9 g, 80 mmol) in 2-butanone (150 ml) was stirred at reflux, under nitrogen, for 5½ days. After cooling to room temperature, the mixture was filtered and the residue washed with methanol (150 ml). The filtrate was concentrated in vacuo and the resultant residue treated with methanol (100 ml) and the solid filtered off and washed thoroughly with methanol. The resultant solid was dried to give the title compound (4.9 g, 60%) as a pale yellow solid.

3-(2-Aminoethyl)-2-(2,6-diisopropylphenylimino)-9,10-dimethoxy-3,4,6,7-tetrahydro-2H-pyrimido[6,1-a]isoquinolin-4-one (3)

A mixture of phthalimide 2 (4.9 g, 8.08 mmol) and hydrazine monohydrate (2.01 g, 40.4 mmol) in chloroform (70 ml) and ethanol (105 ml) was stirred at room temperature, under nitrogen, for 18 h. Additional hydrazine hydrate (0.5 g, 10 mmol) was added and the mixture stirred for a further 3 h. After cooling to 0° C. in an ice/water bath, the solid was removed by filtration, the residue washed with a little cold chloroform and the filtrate concentrated in vacuo. This residue was taken up in dichloromethane and the insoluble material removed by filtration. The filtrate was dried (MgSO$_4$), filtered and concentrated in vacuo to afford the title compound (3.24 g, 84%) as a yellow foam.

3-(N-Carbamoyl-2-aminoethyl)-2-(2,6-diisopropylphenylimino)-9,10-dimethoxy-3,4,6,7-tetrahydro-2H-pyrimido[6,1-a]isoquinolin-4-one Sodium cyanate (0.87 g, 13.4 mmol) in water (20 ml) was added dropwise to a stirred solution of amine 3 (3.2 g, 6.7 mmol) in water (100 ml) and 1M HCl (13.4 ml) at 80° C. After stirring for 4 h at 80° C. the mixture was cooled and basified with 2M NaOH. The mixture was extracted with CH$_2$Cl$_2$ until no more product remained in the organic phase. The organic phases were combined, dried (MgSO$_4$), filtered and concentrated in vacuo. The residue was purified by column chromatography [dichloromethane/methanol (97:3)] and the isolated product taken up in a mixture of dichloromethane and ether which on concentration afforded the title compound (0.6 g, 17%) as a pale yellow foam.

| M.p.: | 213-215° C. | |
|---|---|---|
| m/z: | C$_{29}$H$_{37}$N$_5$O$_4$ requires M = 519, found (M + 1) = 520 | |
| HPLC: | Area | 97.59% |
| | Column | ODS LUNA (150 4.6 mm) |
| | MP | pH 3 KH$_2$PO$_4$/CH$_3$CN gradient 90% aq going to 50% over 25 mins |
| | FR | 1.0 mlmin$^{-1}$ |
| | RT | 10.723 min |
| | Detection | 250 nm |

$^1$H NMR (300 MHz; DMSO): 1.07 (12H, dd, 4 CH$_3$), 2.82-2.94 (4H, m, CH$_2$ and 2 CH(CH$_3$)$_2$, 3.55 (3H, s, OMe), 3.78 (3H, s, OMe), 3.91 (2H, t, CH$_2$), 4.17 (2H, t, CH$_2$), 5.32 (1H, s, vinylic H), 5.45 (2H, br s, NH$_2$), 6.13 (1H, t, NH), 6.56 (1H, s, ArH), 6.95 (1H, s, ArH), 7.00 (1H, m, ArH), 7.10 (1H, s, ArH), 7.12 (1H, br s, ArH).

NB. The proton NMR spectrum above does not show the chemical shift for one CH$_2$ group as it is believed that this signal is obscured by the water signal present in the d$_6$-DMSO at 3.30-3.33.

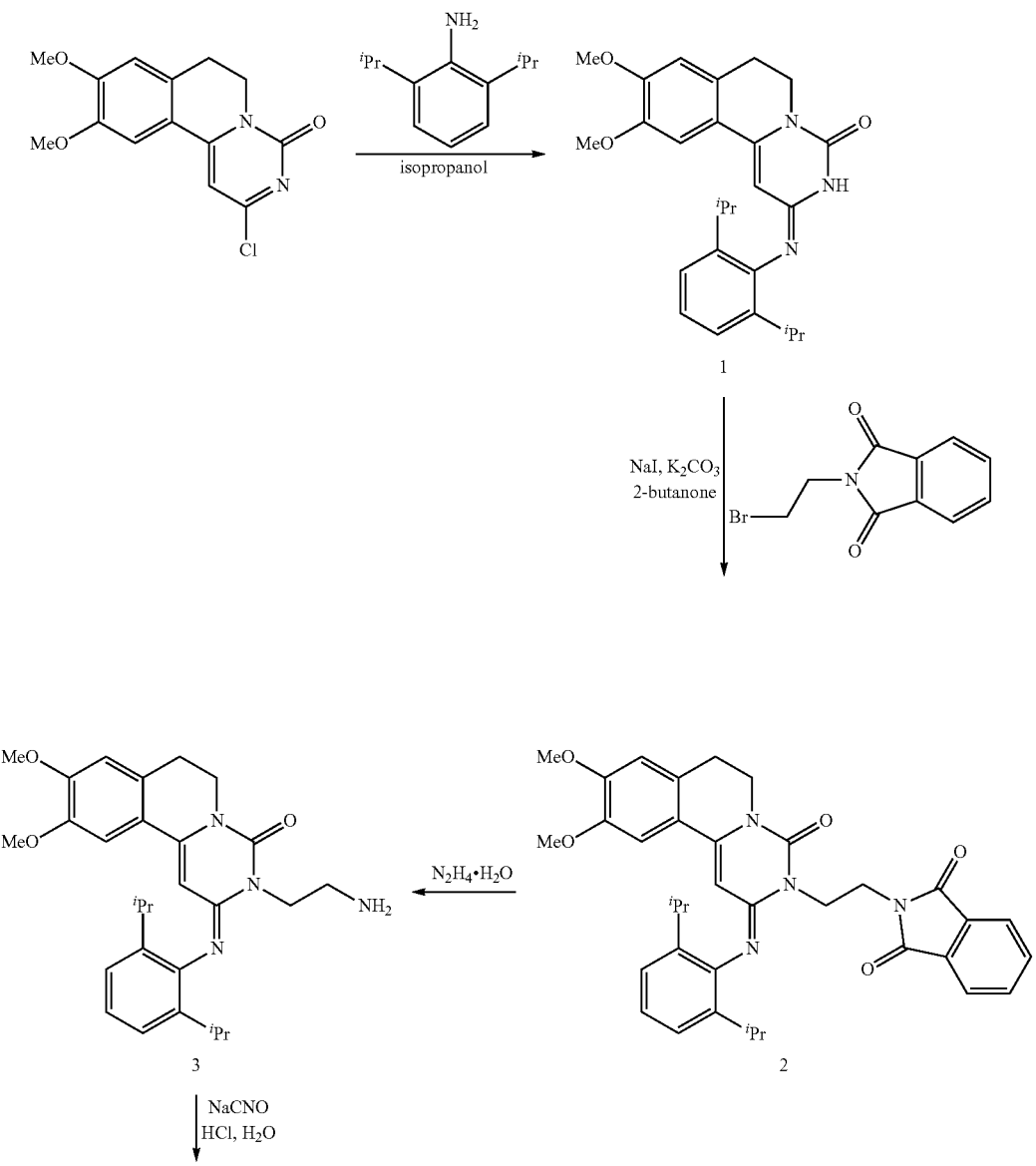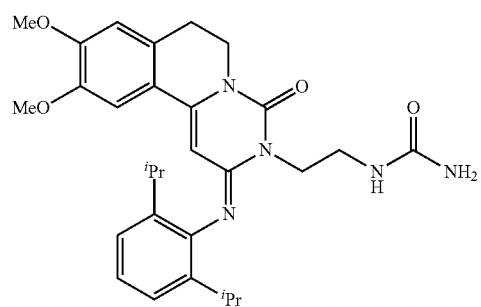

EXAMPLE 12

3-(N-Carbamoyl-4-aminobutyl)-9,10-dimethoxy-2-(2,4,6-trimethylphenylimino)-3,4,6,7-tetrahydro-2H-pyrimido[6,1-a]isoquinolin-4-one

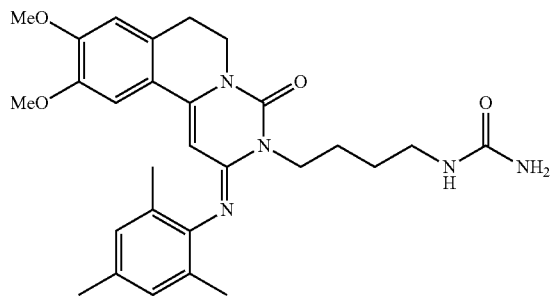

9,10-Dimethoxy-3-(4-N-phthalimidobutyl)-2-(2,4,6-trimethylphenylimino)-3,4,6,7-tetrahydro-2H-pyrimido[6,1-a]isoquinolin-4-one (1)

A mixture of 9,10-dimethoxy-2-(2,4,6-trimethylphenylimino)-3,4,6,7-tetrahydro-2H-pyrimido[6,1-a]isoquinolin-4-one (4.0 g, 10.2 mmol), N-(4-bromobutyl)phthalimide (8.6 g, 30.6 mmol), potassium carbonate (12.7 g, 91.8 mmol) and sodium iodide (4.6 g, 30.6 mmol) in 2-butanone (100 ml) was stirred at reflux, under nitrogen for 4 days. After cooling to room temperature, the solid was removed by filtration and the filtrate was evaporated in vacuo. The residual solid was purified by column chromatography on silica gel [petroleum ether/ethyl acetate (2:1)-(1:1)]. The title compound (1.45 g, 24%) was obtained as a yellow solid.

3-(4-Aminobutyl)-9,10-dimethoxy-2-(2,4,6-trimethylphenylimino)-3,4,6,7-tetrahydro-2H-pyrimido[6,1-a]isoquinolin-4-one (2)

A solution of 1 (1.4 g, 2.36 mmol) in ethanol (30 ml) and chloroform (20 ml) was treated with hydrazine hydrate (0.42 g, 7.09 mmol) and stirred at room temperature, under nitrogen. After 18 h further hydrazine hydrate (0.42 g) was added and stirred for an additional 5 h. The reaction mixture was then cooled to 0° C. and the solid was removed by filtration. The filtrate was dried (MgSO$_4$) and evaporated in vacuo to obtain the title compound (1.0 g, 92%) as a yellow solid.

3-(N-Carbamoyl-4-aminobutyl)-9,10-dimethoxy-2-(2,4,6-trimethylphenylimino)-3,4,6,7-tetrahydro-2H-pyrimido[6,1-a]isoquinolin-4-one Sodium cyanate (0.28 g, 4.32 mmol) in water (6 ml) was added dropwise to a stirred solution of 2 (1.0 g, 2.16 mmol) in water (30 ml) and 1N HCl (4.3 ml) at 80° C. After 2 h at 80° C. the mixture was cooled and extracted with dichloromethane (3×20 ml) and the extract dried (MgSO$_4$) and evaporated in vacuo. The residue was purified by column chromatography on silica gel [dichloromethane/methanol (97:3)] to obtain the title compound (0.70 g, 64%) as a yellow solid.

| M.p: | 234-235° C. | |
|---|---|---|
| M/z | C$_{28}$H$_{35}$N$_5$O$_4$ requires M = 505, found m/z [ES+] = 506 | |
| HPLC: | Area (%) | 98.94 |
| | Column | ODS LUNA 3uC18(2) (100 × 4.6 mm) |
| | MP | 0.02M KH$_2$PO$_4$/CH$_3$CN |
| | | (gradient 90% aq → 50% aq over 25 min) |
| | RT (min) | 17.201 |
| | FR (ml/min) | 1.0 |
| | Detection | 250 nm |

$^1$H NMR (300 MHz, CDCl$_3$): δ 1.64 (2H, m, CH$_2$), 1.90 (2H, m, CH$_2$), 2.07 (6H, s, 2×CH$_3$), 2.26 (3H, s, CH$_3$), 2.92 (2H, t, CH$_2$), 3.30 (2H, m, CH$_2$), 3.73 (3H, s, OCH$_3$), 3.88 (3H, s, OCH$_3$), 4.06 (2H, t, CH$_2$), 4.27 (4H, m, CH$_2$+NH$_2$), 5.44 (1H, s, C═CH), 6.65 (1H, s, ArH), 6.67 (1H, s, ArH), 6.89 (2H, s, 2×ArH).

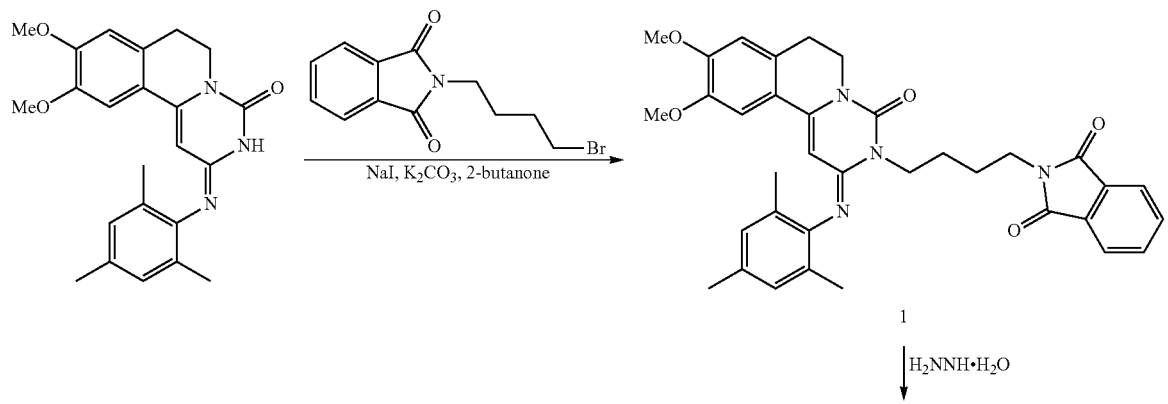

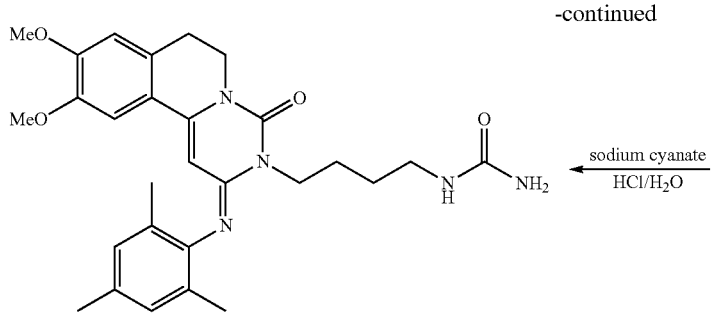
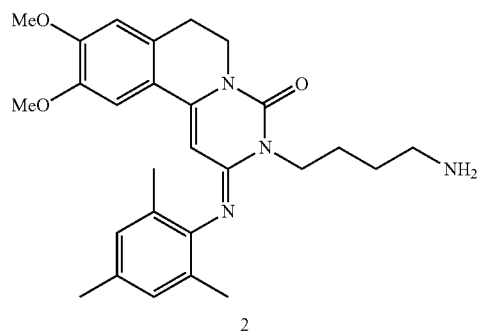

EXAMPLE 13

3-[N—(N'-Cyano-N''-methyl)-2-guanidinoethyl]-9,10-dimethoxy-2-(2,4,6-trimethyl-phenylimino)-3,4,6,7-tetrahydro-2H-pyrimido[6,1-a]isoquinolin-4-one

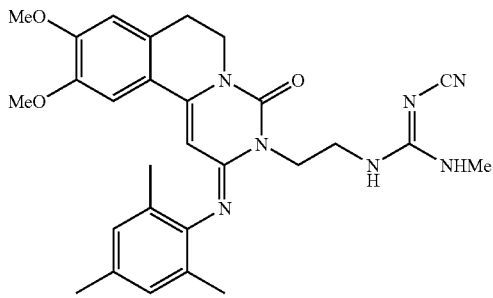

3-[N—(N'-Cyano-S-methyl)-2-isothioureidoethyl]-9,10-dimethoxy-2-(2,4,6-trimethyl-phenylimino)-3,4,6,7-tetrahydro-2H-pyrimido[6,1-a]isoquinolin-4-one (1)

Dimethyl N-cyanodithioiminocarbonate (7.45 g, 46.1 mmol) was added to a solution of 3-(2-aminoethyl)-9,10-dimethoxy-2-(2,4,6-trimethylphenylimino)-3,4,6,7-tetrahydro-2H-pyrimido[6,1-a]isoquinolin-4-one (2.0 g, 4.61 mmol) in toluene (50 ml) and stirred at 90° C. under nitrogen. After 2 h the solvent was evaporated in vacuo and the residue was purified by column chromatography on silica gel [dichloromethane/methanol (100:0)-(95:5)]. The title compound (2.30 g, 94%) was obtained as a yellow solid.

3-[N—(N'-Cyano-N''-methyl)-2-guanidinoethyl]-9,10-dimethoxy-2-(2,4,6-trimethyl-phenylimino)-3,4,6,7-tetrahydro-2H-pyrimido[6,1-a]isoquinolin-4-one A solution of 1 (2.0 g, 3.76 mmol) in dichloromethane (30 ml) was treated with 2M methylamine/THF (9.4 ml, 18.8 mmol) and stirred at reflux, under nitrogen. After 16 h additional 2M methylamine/THF (9.4 ml) was added, followed by a further two portions of 2M methylamine/THF (9.4 ml) at 2 h intervals. After 24 h at reflux the reaction was cooled and evaporated in vacuo. The residue was purified by column chromatography on silica gel [dichloromethane/methanol (98:2)] to obtain, after trituration with ether, the title compound (1.20 g, 62%) as a pale yellow solid.

| M.p.: | 223-224° C. | |
|---|---|---|
| M/z: | $C_{28}H_{33}N_7O_3$ requires M = 515, found m/z [ES+] = 516 | |
| HPLC: | Area (%) | 100 |
| | Column | ODS LUNA 3uC18(2) (100 × 4.6 mm) |
| | MP | 0.02M $KH_2PO_4$/$CH_3CN$ |
| | | (gradient 90% aq → 50% aq over 25 min) |
| | RT (min) | 17.838 |
| | FR (ml/min) | 1.0 |
| | Detection | 250 nm |

$^1$H NMR (300 MHz, CDCl$_3$): δ 1.99 (6H, s, 2×CH$_3$), 2.22 (3H, s, CH$_3$), 2.43 (3H, d, NHCH$_3$), 2.86 (2H, t, CH$_2$), 3.52 (2H, m, CH$_2$), 3.69 (3H, s, OCH$_3$), 3.83 (3H, s, OCH$_3$), 4.02 (2H, t, CH$_2$), 4.28 (2H, m, CH$_2$), 5.39 (1H, s, C=CH), 6.61 (1H, s, ArH), 6.63 (1H, s, ArH), 6.82 (2H, s, 2×ArH).

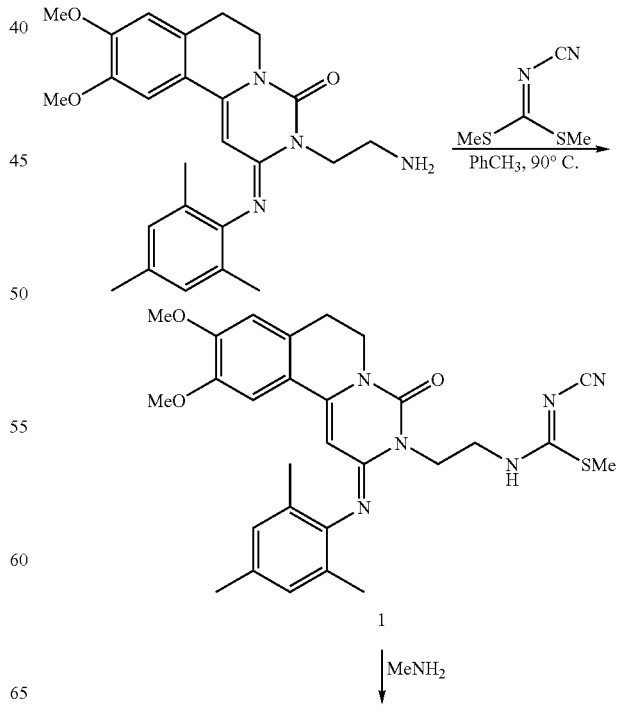

-continued

[Chemical structure: MeO and MeO substituted bicyclic compound with pyrimido-isoquinolinone core, linked via N-CH2CH2-NH-C(=NCN)-NHMe guanidine group, and N=aryl (2,4,6-trimethylphenyl) imino substituent]

The pharmacological utility of the compounds of the present invention has been demonstrated in studies using compounds previously synthesised from the above Examples. The results below serve to illustrate the generic application of the compounds of the present invention.

EXAMPLE A

Efficacy of a Compound of the Invention Against Electrical-Induced Contraction of Guinea-Pig Isolated Trachea The efficacy of the compounds of Example 1, 8, 9, 10, 11 and 13 were tested against electrical-induced contraction of guinea-pig isolated trachea. The results demonstrate that the compounds of the present invention inhibit the contractile responses with a long duration of action.

Method

Superfusion of guinea-pig tracheal rings was performed according to a previously described method (Coleman et al. 1996; Pulmonary Pharmacology, 9, 107-117). Briefly, guinea-pig tracheal preparations were cut into rings then opened by sectioning the ring opposite the smooth muscle and suspended between two platinum electrodes under 1 g tension. The tissues were superfused at a rate of 3.25 mL/min with Krebs-Henseleit solution at 37° C. containing the cyclooxygenase inhibitor, indomethacin (5 µM) and bubbled with 95% $O_2$ and 5% $CO_2$. Tracheal preparations were allowed to equilibrate for 40 min before commencement of electrical stimulation delivered as a 10 s train of square wave pulses at 3 Hz, 0.1 ms duration and 20V (approx. 400 mAmps) generated every 100 sec by means of physiological square wave-stimulator.

The compound of Example 1 was dissolved in DMSO containing Tween 80 (10%) and distilled water (0.01M), which were then added to the organ bath to give a final concentration of 10 µM. The other compounds were prepared in DMSO and diluted in Krebs-Henseleit solution which yielded a final superfusion concentration of 0.05% DMSO, and superfused at a rate of 0.3 ml/min; contractile responses to electrical field stimulation was recorded on a Macintosh computer using MacLab software.

Results

The vehicle, DMSO, failed to significantly inhibit the contractile response to electrical field stimulation (FIG. 2). The results for the compounds are shown in Figures: 3 for compound of Example 1; 4 for compound of Example 9; 5 for compound of Example 10; 6 for compound of Example 11; 7 for compound of Example 13; and 8 for compound of Example 8.

The compounds caused complete inhibition of the contractile response to electrical field stimulation and the effect was maintained for more than 2-4 hours.

EXAMPLE B

Efficacy of a Compound of the Invention Against Proliferation of Human Mononuclear Cells Stimulated by PHA The effect of the compound of Example 1, 9,10-Dimethoxy-2-(2,4,6-trimethylphenylimino)-3-(N-carbamoyl-2-aminoethyl)-3,4,6,7-tetrahydro-2H-pyrimido[6,1-a] isoquinolin-4-one, against proliferation of human mononuclear cells stimulated by PHA was investigated. Proliferation was significantly inhibited by the compound, indicating that it possesses anti-inflammatory activity. The result below serves to illustrate the generic application of the novel compounds of the present invention.

Method

Normal healthy volunteers underwent phlebotomy and 25 ml of blood was collected. Mononuclear cells were separated and purified according to the method of Banner et al. (Banner et al. *Br. J. Pharmacol.* 116 3169-3174 (1995)). Human peripheral mononuclear cells (100,000 per well) were stimulated for 24 h with phytohaemagglutinin (PHA, 2 µg/ml) in the absence or presence of the compound of Example 1 (0.001-100 µM) at 37° C. in a 95% air, 5% $CO_2$ atmosphere. Twenty four hours later, [$^3$H]-thymidine (0.1 µCi) was added to each well and the cells were incubated for a further 24 h period. Cells were then harvested onto glass fibre filters using a cell harvester (ICN Flow, Buckinghamshire) and counted in a scintillation counter.

Results

The compound under test caused a concentration dependent inhibition of the proliferation of human mononuclear cells stimulated with PHA (number of experiments is 6; FIG. 8). The $IC_{50}$ values and 95% confidence limits for these compounds are indicated in Table 1. The result is also shown in the graph of FIG. 8.

TABLE 1

$IC_{50}$ value for the compound of Example 1 against proliferation of human mononuclear cells stimulated with PHA

| Compound from | $IC_{50}$ | n |
|---|---|---|
| Example 1 | 0.46 µM (0.239-0.897) | 6 |

EXAMPLE C

Inhibition of Phosphodiesterase (PDE) Type 3 and 4 Isozymes

The compound of Example 1, 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one, has been shown to be a potent inhibitor of phosphodiesterase (PDE) type 3 and 4 isozymes. The $IC_{50}$ values are shown below.

|  | PDE3 (nM) (human platelet) | PDE4 (nM) (human neutrophil) |
|---|---|---|
| Compound of Example 1 | 0.43 | 1479 |
| Rolipram | ND | 6412 |
| Cilostamide | 89 | ND |

Rolipram is a known PDE 4 inhibitor and cilostamide is a known PDE 3 inhibitor
ND—Not determined

EXAMPLE D

Effect of the Compound of Example 1,9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one, on LPS Induced TNF-α Release from Human Monocytes

|  | IC50 (nM) |
| --- | --- |
| Compound of Example 1 | 7.5 n = 6 |
| CDP 840 (PDE4 inhibitor) | 92 n = 6 |
| Siguazodan (PDE3 inhibitor) | >100 µM |

EXAMPLE E

In Vivo Tests

1. The compound of Example 1, 9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one, was tested in a model of histamine induced bronchospasm. Conscious guinea-pigs were exposed to dry powder (micronised) compound. The drug was blended with lactose so that the final concentration was 0.25, 2.5 and 25%. At various times after exposure to drug the animals were anaesthetised and challenged with varying doses of histamine. Total airway resistance and mean arterial blood pressure were recorded.

Exposure to dry powder (2.5 and 25%) provided significant protection against histamine induced bronchospasm over a 5.5 hour period and reduced mean blood pressure over this period.

2. Intravenous administration of the compound (1 to 100 µg/kg) to urethane anaesthetised guinea-pigs produced a dose dependant reduction in mean arterial blood pressure. The compound was dissolved in DMSO then diluted with saline (there was evidence that the compound had come out of solution).

3. In a model of antigen induced eosinophilia in the ovalbumin sensitised guinea-pig, the compound (10 mg/kg) administered orally 1 hour prior to antigen challenge, significantly inhibited the recruitment of eosinophils to the lungs following antigen challenge (aerosol) in sensitised guinea-pigs. Exposure to dry powder (25%), 1.5 hours prior to antigen challenge, significantly inhibited recruitment of eosinophils to the lungs (measurements were made 24 hours after challenge).

Further experiments were carried out to characterise the duration of action in this model. Compound (25%) administration 5.5 hours before antigen challenge failed to significantly inhibit eosinophil recruitment to the lungs.

EXAMPLE F

Taste of Compounds

For pharmaceutical compounds which are administered orally, taste is a very important factor in ensuring patient compliance. Unexpectedly, the compounds of the present invention are substantially tasteless. They are therefore particularly suitable for oral administration, for example as dry powder to be inhaled.

Method

Small amounts of the compound of Example 1, trequinsin (9,10-dimethoxy-3-methyl-2-mesitylimino-2,3,6,7-tetrahydro-4H-pyrimido[6,1-a]isoquinolin-4-one) and desmethyl trequinsin (9,10-dimethoxy-2-mesitylimino-2,3,6,7-tetrahydro-4H-pyrimido[6,1-a]isoquinolin-4-one) were placed on the tip of the tongue of an informed, healthy male volunteer and the taste of each compound was assessed.

Results

The results, displayed in Table 3 below, show that the compound of Example 1 has significantly improved taste compared with trequinsin or desmethyl trequinsin.

| Compound (from) | Taste[1] |
| --- | --- |
| Example 1 | *** |
| Trequinsin | * |
| Desmethyl trequinsin | * |

[1]Scale: * Very bitter  Bitter * Tasteless

The invention claimed is:

1. A compound of formula I:

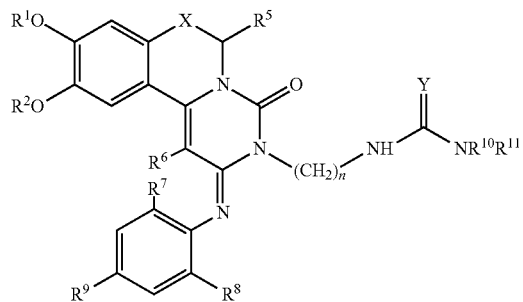

wherein
each of $R^1$ and $R^2$ independently represents a $C_{1-6}$ alkyl or $C_{2-7}$ acyl group;
$R^5$ represents a hydrogen atom or a $C_{1-3}$ alkyl, $C_{2-3}$ alkenyl or $C_{2-3}$ alkynyl group;
$R^6$ represents a hydrogen atom or a $C_{1-6}$ alkyl, $C_{2-6}$ alkenyl, $C_{2-6}$ alkynyl, amino, $C_{1-6}$ alkylamino, di($C_{1-6}$)alkylamino or $C_{2-7}$ acylamino group;
each of $R^7$ and $R^8$ independently represents a hydrogen or halogen atom or a hydroxy, trifluoromethyl, $C_{1-6}$ alkyl, $C_{2-6}$ alkenyl, $C_{2-6}$ alkynyl, $C_{2-7}$ acyl, $C_{1-6}$ alkylthio, $C_{1-6}$ alkoxy, $C_{3-6}$ cycloalkyl; and
$R^9$ represents a hydrogen or halogen atom or a hydroxy, trifluoromethyl, $C_{1-6}$ alkyl, $C_{2-4}$ alkenyl, $C_{2-6}$ alkynyl, $C_{2-7}$ acyl, $C_{1-6}$ alkylthio, $C_{1-6}$ alkoxy or $C_{3-6}$ cycloalkyl group; X represents a group $CR^3R^4$, wherein each of $R^3$ and $R^4$ independently represents a hydrogen atom or a $C_{1-3}$ alkyl group;
each of $R^{10}$ and $R^{11}$ independently represents a hydrogen atom, a $C_{1-3}$ alkyl, $C_{3-6}$ cycloalkyl or phenyl group;
Y represents an oxygen atom or a group $CHNO_2$, NCN, NH or $NNO_2$; n is an integer from 2 to 4; or a salt thereof.

2. The compound of claim 1, wherein, independently or in any compatible combination:
each of $R^1$ and $R^2$ represents a $C_{1-6}$ alkyl;
$R^1$ and $R^2$ are the same as each other;
each of $R^3$ and $R^4$ represents a hydrogen atom;
$R^5$ represents a hydrogen atom;
$R^6$ represents a hydrogen atom;
each of $R^7$ and $R^8$ represents a $C_{1-6}$ alkyl;

R⁷ and R⁸ are the same as each other;
R⁹ represents a halogen atom or a methyl or acetyl group;
Y represents an oxygen atom or a group CHNO₂; and n is 2.

3. The compound of claim 2, wherein each of $R^1$ and $R^2$ represents a $C_{1-4}$ alkyl, group; and each of $R^7$ and $R^8$ represents a methyl, ethyl or isopropyl group.

4. A composition comprising a compound of formula I:

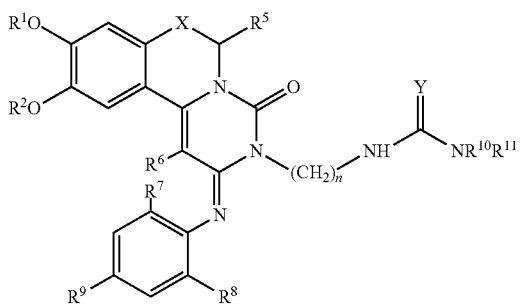

wherein
each of $R^1$ and $R^2$ independently represents a $C_{1-6}$ alkyl or $C_{2-7}$ acyl group;
$R^5$ represents a hydrogen atom or a $C_{1-3}$ alkyl, $C_{2-3}$ alkenyl or $C_{2-3}$ alkynyl group;
$R^6$ represents a hydrogen atom or a $C_{1-6}$ alkyl, $C_{2-6}$ alkenyl, $C_{2-6}$ alkynyl, amino, $C_{1-6}$ alkylamino, di($C_{1-6}$)alkylamino or $C_{2-7}$ acylamino group;
each of $R^7$ and $R^8$ independently represents a hydrogen or halogen atom or a hydroxy, trifluoromethyl, $C_{1-6}$ alkyl, $C_{2-6}$ alkenyl, $C_{2-6}$ alkynyl, $C_{2-7}$ acyl, $C_{1-6}$ alkylthio, $C_{1-6}$ alkoxy, $C_{3-6}$ cycloalkyl; and
$R^9$ represents a hydrogen or halogen atom or a hydroxy, trifluoromethyl, $C_{1-6}$ alkyl, $C_{2-4}$ alkenyl, $C_{2-6}$ alkynyl, $C_{2-7}$ acyl, $C_{1-6}$ alkylthio, $C_{1-6}$ alkoxy or $C_{3-6}$ cycloalkyl group; X represents a group $CR^3R^4$, wherein each of $R^3$ and $R^4$ independently represents a hydrogen atom or a $C_{1-3}$ alkyl group;
each of $R^{10}$ and $R^{11}$ independently represents a hydrogen atom, a $C_{1-3}$ alkyl, $C_{3-6}$ cycloalkyl or phenyl group;
Y represents an oxygen atom or a group CHNO₂, NCN, NH or NNO₂; n is an integer from 2 to 4; or a salt thereof, and a veterinarily or pharmaceutically acceptable carrier or diluent.

5. The composition of claim 4, wherein
each of $R^1$ and $R^2$ represents a $C_{1-6}$ alkyl;
$R^1$ and $R^2$ are the same as each other;
each of $R^3$ and $R^4$ represents a hydrogen atom;
$R^5$ represents a hydrogen atom;
$R^6$ represents a hydrogen atom;
each of $R^7$ and $R^8$ represents a $C_{1-6}$ alkyl;
$R^7$ and $R^8$ are the same as each other;
$R^9$ represents a halogen atom or a methyl or acetyl group;
Y represents an oxygen atom or a group CHNO₂; and n is 2.

6. The composition of claim 5, wherein each of $R^1$ and $R^2$ represents a $C_{1-4}$ alkyl, group; and each of $R^7$ and $R^8$ represents a methyl, ethyl or isopropyl group.

7. The composition of claim 4, wherein the composition is a pharmaceutical composition for human medicine.

8. The composition of claim 7, adapted for administration by aerosol.

* * * * *